US009376686B2

(12) United States Patent
Campos-Neto et al.

(10) Patent No.: US 9,376,686 B2
(45) Date of Patent: Jun. 28, 2016

(54) VACCINE AND THERAPEUTIC DELIVERY SYSTEM

(71) Applicants: Antonio Campos-Neto, Westborough, MA (US); Mark Cayabyab, San Jose, CA (US); Margaret Duncan, Brookline, MA (US)

(72) Inventors: Antonio Campos-Neto, Westborough, MA (US); Mark Cayabyab, San Jose, CA (US); Margaret Duncan, Brookline, MA (US)

(73) Assignee: Forsyth Dental Infirmary for Children, Cambridge, MA (US)

( * ) Notice: Subject to any disclaimer, the term of this patent is extended or adjusted under 35 U.S.C. 154(b) by 0 days.

(21) Appl. No.: 13/624,146

(22) Filed: Sep. 21, 2012

(65) Prior Publication Data

US 2013/0095131 A1    Apr. 18, 2013

Related U.S. Application Data

(60) Provisional application No. 61/538,346, filed on Sep. 23, 2011.

(51) Int. Cl.
| | |
|---|---|
| *A61K 39/09* | (2006.01) |
| *A61K 39/21* | (2006.01) |
| *A01N 63/00* | (2006.01) |
| *C12P 21/04* | (2006.01) |
| *C12N 15/74* | (2006.01) |
| *C07K 14/00* | (2006.01) |
| *C07K 14/155* | (2006.01) |
| *C07K 14/16* | (2006.01) |
| *C07K 14/35* | (2006.01) |
| *C07K 14/005* | (2006.01) |
| *C07K 14/315* | (2006.01) |

(52) U.S. Cl.
CPC ............... *C12N 15/74* (2013.01); *C07K 14/00* (2013.01); *C07K 14/005* (2013.01); *C07K 14/155* (2013.01); *C07K 14/162* (2013.01); *C07K 14/315* (2013.01); *C07K 14/35* (2013.01); *C12N 2740/15022* (2013.01); *C12N 2740/15033* (2013.01); *C12N 2740/16033* (2013.01); *C12N 2740/16122* (2013.01)

(58) Field of Classification Search
None
See application file for complete search history.

(56) References Cited

U.S. PATENT DOCUMENTS 5,821,088 A * 10/1998 Darzins et al. ............... 435/69.7

FOREIGN PATENT DOCUMENTS

| WO | WO-88/05823 A2 | 8/1988 |
| WO | WO-93/18163 A2 | 9/1993 |
| WO | WO 2004072093 A2 * | 8/2004 |

OTHER PUBLICATIONS

Pozzi et al., "Delivery and expression of a heterologous antigen on the surface of streptococci," Infection and Immunity, vol. 60, No. 5: pp. 1902-1907 (1992).*

(Continued)

*Primary Examiner* — Benjamin P Blumel
*Assistant Examiner* — M. Franco Salvoza
(74) *Attorney, Agent, or Firm* — Foley Hoag LLP

(57) ABSTRACT

The present invention relates to a new vaccine delivery system. In particular, the present invention includes compositions and methods of integrally transformed non-pathogenic, commensal bacteria that can express a nucleic acid molecule of a foreign polypeptide, wherein the nucleic acid molecule that encodes the foreign polypeptide is stably integrated into genomic DNA of the bacteria. The foreign polypeptide includes a vaccine antigen that elicits an immunogenic response, an inhibitor of a pathogen, or an immune booster or modulator.

5 Claims, 35 Drawing Sheets

Mean percentage DNA probe count for samples from human oral cavity in 225 healthy subjects *(adapted from Mager, DL, Ximenez-Fyvie, LA, Haffajee, AD & Socransky, SS. J Clin Periodontol 2003; 30: 644–654)*

(56) References Cited

OTHER PUBLICATIONS

Mitchell et al., "Mechanism of cell surface expression of the *Streptococcus mitis* platelet binding proteins PblA and PblB," Molecular Microbiology 64(3): pp. 844-957 (2007).*

Erra-Pujada et al. ("The Type II Pullanase of Thermococcus hydrothermalis," J. Bacteriol., 181 (10): pp. 3284-3287 (1999).*

Pozzi et al. "Expression of M6 Protein Gene of *Streptococcus pyogenes* in *Streptococcus gordonii* After Chromosomal Integration and Transcriptional Fusion" Infection and Immunity (1992) 143:449-457.*

Takamatsu et al., "Binding of the *Streptococcus gordonii* surface glycoproteins GspB and Has to specific carbohydrate structures on platelet membrane glycoprotein Ibα," Molecular Microbiology 58(2): pp. 380-392 (2005).*

Ronda et al., "Characterization of genetic transformation in *Streptococcus oralis* NCTC 11427: Expression of the pneumococcal amidase in *S. oralis* using a new shuttle vector," Mol Gen Genet 215: 53-57 (1988).*

Zahnder et al., "Mitis Group Streptococci Express Variable Pilus Islet 2 Pili," PLoS One 6(9): e25124 (2011).*

Denapaite et al., "The Genome of *Streptococcus mitis* B6—What Is a Commensal?" PLoS One 5(2): e9426 (2010).*

Cvitokovitch, "Genetic Competence and Transformation in Oral Streptococci," Crit Rev Oral Biol Med 12(3): 217-243 (2001).*

Waterhouse et al., "Dispensable genes and foreign DNA in *Streptococcus mutans*," Microbiology 152: 1777-1788 (2006).*

Kirchherr, Jennifer L., et al., "Clonal Diversity and Turnover of *Streptococcus mitis* by 1 on Shedding and Nonshedding Oral Surfaces of Human Infants during the First Year of Life," Clin. Diagn. Lab. Immunol. 12(10): 1184-1190 (2005).

Van Der Poll, T et al.; "Interleukin-6 gene-deficient mice show impaired defense against pneumoccocal pneumonia," J. Infect. Dis., 176(2): 439-444 (1997).

Walker, GJ. "Metabolism of the reserve polysaccharide of *Streptococcus mitis*, Some properties of a pullulanase," Biochem J., 108(1): 33-40 (1968) (especially abstract).

Wyatt, Richard et al. "The antigenic structure of the HIV gp120 envelope glycoprotein," Nature, 393: 705-711 (1998). (Especially abstract).

International Search Report for PCT/US2012/056616 mailed Dec. 25, 2014.

* cited by examiner

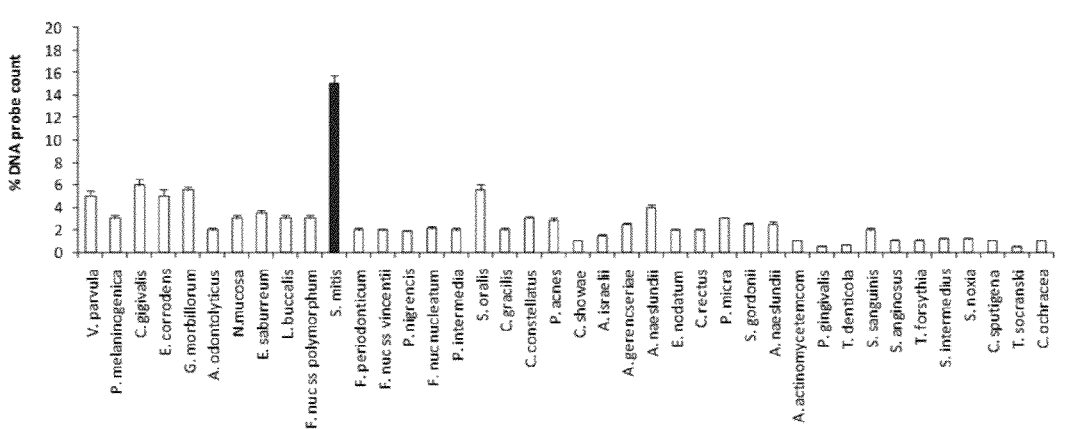
Fig. 1. Mean percentage DNA probe count for samples from human oral cavity in 225 healthy subjects *(adapted from Mager, DL, Ximenez-Fyvie, LA, Haffajee, AD & Socransky, SS. J Clin Periodontol 2003; 30: 644–654)*

Fig. 2. Strategy for expressing HIV or Mtb antigens

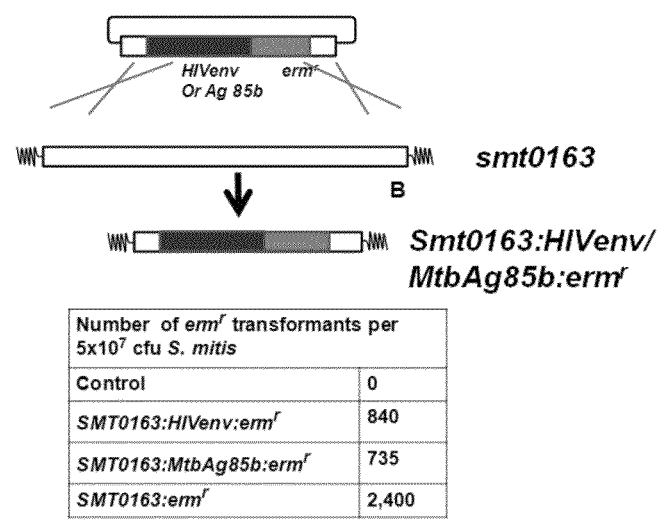
Fig. 3. Transformation of S. mitis

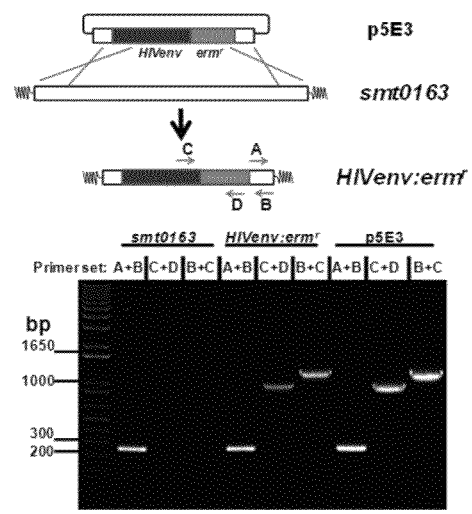
Fig. 4. Integration of foreign HIV gene in *S. mitis*

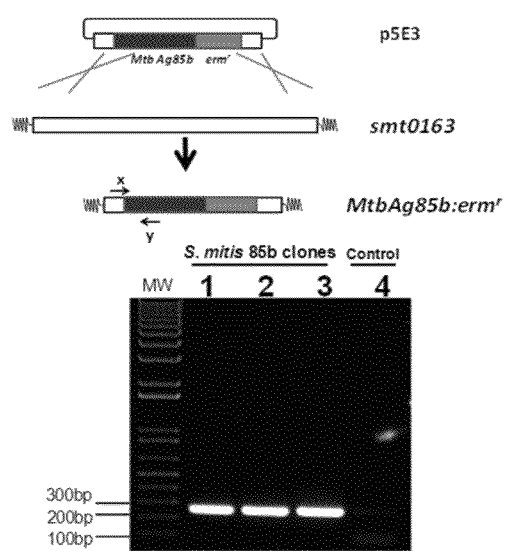
Fig. 5. Integration of foreign Mtb gene in *S. mitis*

Recombinant *S. mitis* expresses HIV-1 gp 120 antigen

Number of Erm$^r$ colonies/total no. of colonies streaked

| rS. mitis clone | No. of generations | | | | |
|---|---|---|---|---|---|
| | 6 | 12 | 18 | 24 | 30 |
| HIVgp120A | 120/120 | 142/142 | 108/108 | 139/139 | 119/119 |
| HIVgp120B | 115/115 | 131/131 | 117/117 | 123/123 | 145/145 |
| HIVgp120C | 130/130 | 109/109 | 143/143 | 118/118 | 138/138 |
| HIVgp120D | 123/123 | 136/136 | 148/148 | 108/108 | 114/114 | rSmitis HIVgp120 generations
Control  0  30 rS. mitis is stable

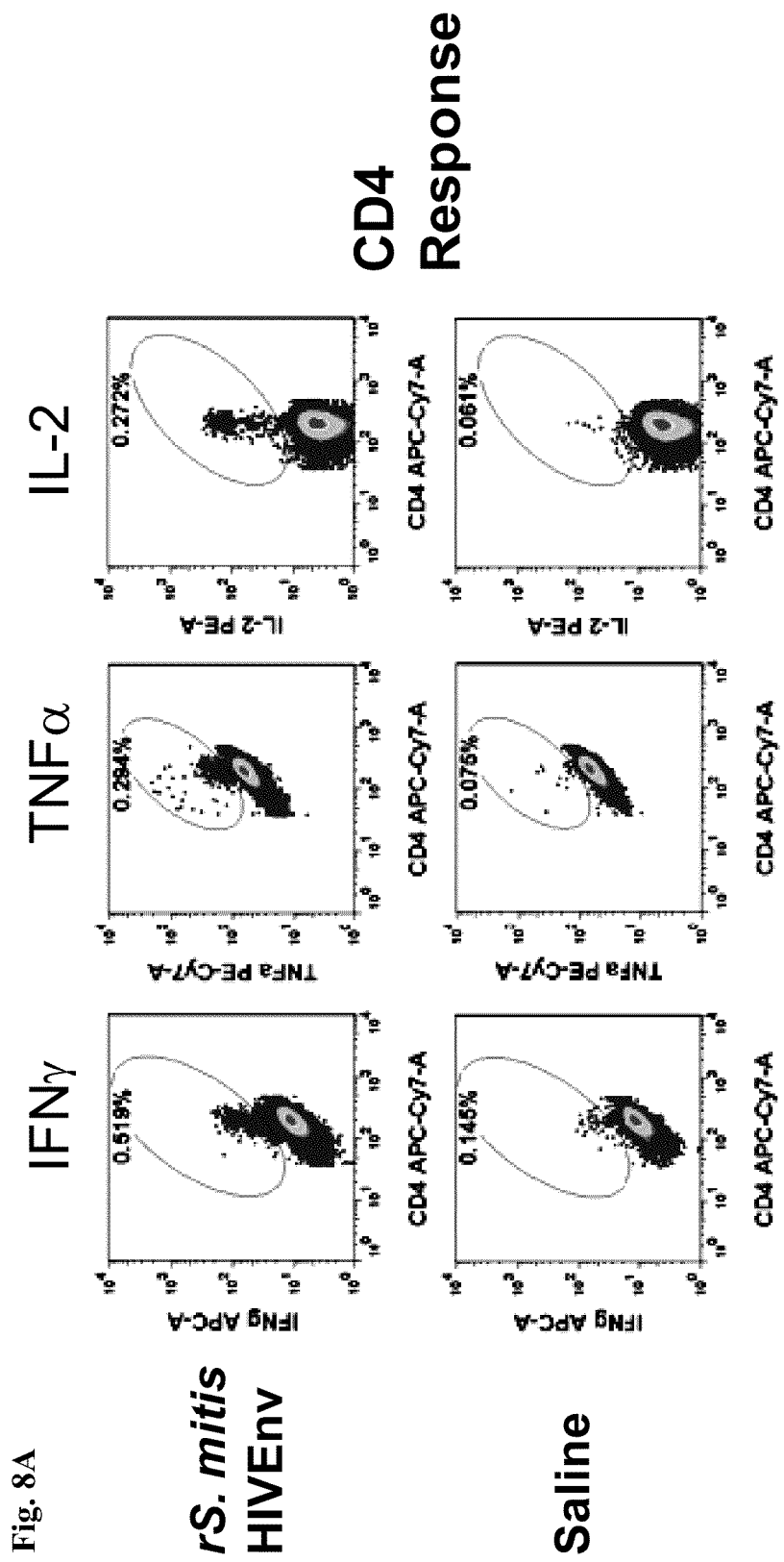

Vaccine elicited *S. mitis*-specific T cell responses in mice

Protein Sequence

SEQ ID NO: 2 - DGYVGAPAH
>MT0401
MIDGWTEEQHEPTVRHERPAAPQDVRRVMLLGSAEPSRELAIALQGLGAEVIAV
<u>DGYVGAPAH</u>RIADQSVVVTMTDAEELTAVIRRLQPDFLVTVTAAVSVDALDAVEQADGECTELVPNARAVRCTADR
EGLRRLAADQLGLPTAPFWFVGSLGELQAVAVHAGFPLLVSPVAGVAGQG
SSVVAGPNEVEPAWQRAAGHQVQPQTGGVSPRVCAESVVEIEFLVTMIVVCSQGPNGPLI
EFCAPIGHRDADAGELESWQPQKLSTAALDAAKSIAARIVKALGGRGVFGVELMINGDEV
YFADVTVCPAGSAWVTVRSQRLSVFELQARAILGLAVDTLMISPGAARVINPDHTAGRAA
VGAAPPADALTGALGVPESDVVIFGRGLGVALATAPEVAIARERAREVASRLNVPDSRE
(SEQ ID NO: 4)

DNA Sequence

SEQ ID NO: 1 - GACGGCTATGTCGGCGCGCCTGCCCAC
>MT0401
GTGATCGACGGCTGGACGGAAGAACAGCACGAACCCACCGTTAGGCATGAGCGCCCAGCA
GCTCCCCAAGACGTTCGGCGGGTGATGTTGCTGGGTTCGGCCGAACCCAGCCGGGAGCTG
GCGATCGCGTTGCAGGGCTTGGGCGCGGAGGTGATCGCCGTC<u>GACGGCTATGTCGGCGCGCCTGCCCACC</u>
GGATAGCCGACCAGTCGGTGGTGGTCACCATGACCGATGCTGAAGAGCTGACGGCGGTGATCCGGCGGCTG
CAACCGGATTTCTTGGTGACGGTCACCGCCGCGGTGTCTGTGGATGCTCTCGATGCCGTCGAGCAAGCCGAC
GGCGAGTGCACTGAGCTGGTGCCGAACGCCCGTGCCGTCCGGTGCACGGCCGACCGGGAGGGCCTGCGCC
GGCTGGCCGCCGATCAGCTCGGCCTGCCCACAGCCCCGTTCTGGTTCGTCGGATCCCTTGGCGAACTTCAAG
CGGTGGCCGTCCATGCTGGGTTTCCGTTGCTGGTGAGCCCGGTGGCAGGGGTGGCTGGCCAGGGTAGCTCG
GTGGTCGCCGGGCCCAACGAGGTCGAGCCCGCCTGGCAGCGCGCGGCAGGCCATCAAGTACAGCCGCAGA
CTGGGGGAGTGAGCCCTCGGGTGTGCGCCGAGTCGGTGGTCGAGATCGAGTTTTTGGTCACCATGATCGTTG
TGTGCAGTCAGGGCCCGAACGGGCCGCTCATCGAGTTCTGTGCACCTATCGGTCATCGCGACGCCGATGCC
GGTGAGTTGGAATCCTGGCAACCGCAGAAGCTGAGCACGGCGGCGCTGGACGCGGCCAAGTCGATCGCCGC
GCGCATCGTCAAGGCGCTCGGGGGACGCGGGGTTTTCGGCGTCGAATTGATGATCAACGGCGATGAGGTGT
ATTTCGCCGATGTCACCGTGTGTCCTGCCGGGAGTGCCTGGGTCACCGTGCGCAGCCAGCGGCTTTCGGTGT
TCGAACTGCAGGCCCGGGCGATCCTGGGTCTGGCGGTGGACACCCTGATGATCTCGCCGGGTGCCGCGCG
GGTGATCAACCCGGACCACACGGCAGGCCGGGCAGCGGTCGGCGCCGCACCACCTGCCGATGCGCTGACC
GGTGCGCTCGGTGTGCCGGAAAGCGACGTCGTGATATTCGGCCGCGGGCTTGGGGTGGCGCTGGCCACCG
CACCCGAGGTGGCAATCGCCCGCGAACGCGCCCGCGAAGTTGCATCTCGGCTAAATGTGCCAGACTCACGC
GAGTGA (SEQ ID NO: 3)

Fig. 10A

Protein Sequence

SEQ ID NO: 6 - LAAVVGVVLAQVL

>Mb0073
MLFAALRDMQWRKRRLVITIISTGLIFGMTLVLTGLANGFRVEARHTVDSMGVDVFVVRS
GAAGPFLGSIPFPDVDLARVAAEPGVMAAAPLGSVGTIMKEGTSTRNVTVFGAPEHGPGM
PRVSEGRSPSKPDEVAASSTMGRHLGDTVEVGARRLRVVGIVPNSTALAKIPNVFLTTEG
LQKLAYNGQPNITSIGIIGMPRQLPEGYQTFDRVGAVNDLVRPLKVAVNSISIVAVLLWI
VAVLIVGSVVYLSALERLRDFAVFKAIGTPTRSIMAGLALQALVIAL<u>LAAVVGVVLAQVL</u>
APLFPMIVAVPVGAYLALPVAAIVIGLFASVAGLKRVVTVDPAQAFGGP (SEQ ID NO: 8)

DNA Sequence

SEQ ID NO: 5 - CTTGCGGCGGTGGTGGGCGTCGTCCTGGCGCAGGTGTTG

>Mb0073
ATGCTCTTCGCGGCCCTGCGTGACATGCAATGGAGAAAGCGCCGCCTGGTCATCACGATC
ATCAGCACCGGGCTGATCTTCGGGATGACGCTTGTTTTGACCGGACTCGCGAACGGCTTC
CGGGTGGAGGCCCGGCACACCGTCGATTCCATGGGTGTCGATGTATTCGTCGTCAGATCC
GGCGCTGCTGGACCTTTTCTGGGTTCAATACCGTTTCCCGATGTTGACCTGGCCCGAGTG
GCCGCTGAACCCGGTGTCATGGCCGCGGCCCCGTTGGGCAGCGTGGGGACGATCATGAAA
GAAGGCACGTCGACGCGAAACGTCACGGTCTTCGGCGCGCCCGAGCACGGACCTGGCATG
CCACGGGTCTCAGAGGGTCGGTCACCGTCGAAACCGGACGAAGTCGCGGCATCGAGCACG
ATGGGCCGACACCTCGGTGACACTGTCGAGGTCGGCGCGCGCAGATTGCGGGTCGTTGGC
ATTGTGCCGAATTCCACCGCGCTGGCCAAGATCCCCAATGTCTTCCTCACGACCGAGGGC
TTACAGAAATTGGCGTACAACGGGCAGCCGAATATCACGTCCATCGGGATCATAGGTATG
CCCCGACAGCTGCCGGAGGGTTACCAGACTTTCGATCGGGTGGGCGCTGTCAATGATTTG
GTGCGCCCATTGAAGGTCGCAGTGAATTCGATCTCGATCGTGGCTGTTTTGCTGTGGATT
GTGGCGGTGCTGATCGTCGGCTCGGTGGTGTACCTTTCGGCTCTTGAGCGGCTACGTGAC
TTCGCGGTGTTCAAGGCGATTGGCACGCCAACGCGCTCGATTATGGCCGGGCTCGCATTA
CAGGCGCTGGTCATTGCGTTG<u>CTTGCGGCGGTGGTGGGCGTCGTCCTGGCGCAGGTGTTG</u>
GCACCACTGTTTCCGATGATTGTCGCGGTACCCGTCGGTGCTTACCTGGCGCTACCGGTG
GCCGCGATCGTCATCGGTCTGTTCGCTAGTGTTGCCGGATTGAAGCGCGTGGTGACGGTC
GATCCCGCGCAGGCGTTCGGAGGTCCCTAG (SEQ ID NO: 7)

Fig. 10B

Protein Sequence

SEQ ID NO: 10 - RSGAATPVR

>MT2160.1
MPAAPSTREKDCMLVLHGFWSNSGGMRLWAEDSDLLVKSPSQALRSGAATPVRGAR (SEQ ID NO: 12)

DNA Sequence

SEQ ID NO: 9 - CGCTCCGGCGCGGCCACACCCGTTCGC

>MT2160.1
GTGCCGGCCGCTCCGTCGACAAGAGAGAAGGACTGCATGCTGGTTTTGCACGGCTTCTGG
TCCAACTCCGGCGGGATGCGGCTGTGGGCGGAGGACTCCGATCTGCTGGTGAAGAGCCCG
AGTCAGGCGCTGCGCTCCGGCGCGGCCACACCCGTTCGCGGCGCCCGCTGA (SEQ ID NO: 11)

Fig. 10C

Protein Sequence

SEQ ID NO: 14 - TCLPFAL

>MT0910.2
MSAPPAQAPVCGALAARPTAPGNASCTRPAKRDCRYGSRCETCLPFALAKDCRQASSRLQ
AATEPDETTTTSVISMRSPGSLQYQPAT (SEQ ID NO: 16)

DNA Sequence

SEQ ID NO: 13 - ACCTGCCTCCCATTCGCACTA

>MT0910.2
ATGTCCGCGCCACCCGCTCAAGCGCCGGTATGTGGCGCCTTGGCGGCTAGGCCAACCGCC
CCCGGCAACGCCAGCTGCACACGCCCAGCGAAGCGCGATTGTCGGTACGGGTCGCGCTGC
GAA<u>ACCTGCCTCCCATTCGCACTA</u>GCAAAAGACTGTCGACAAGCGAGCAGTCGACTTCAG
GCCGCGACCGAACCCGACGAGACGACAACAACATCTGTCATCTCAATGCGCTCACCAGGA
TCGCTACAATATCAGCCAGCTACATGA (SEQ ID NO: 15)

Fig. 10D

Protein Sequence

SEQ ID NO: 18 - TTMPLFAD

>Mb1654c
MPEVTREEPAIDGWFTTDKAGNPHLLGGKCPQCGTYVFPPRADNCPNPACGSDTLESVGL
STRGKLWSYTENRYAPPPPYPAPDPFEPFAVAAVELADEGLIVLGKVVDGTLAADLKVGM
EMELTTMPLFADDDGVQRIVYAWRIPSRAGDDAERSDAEERRR (SEQ ID NO: 20)

DNA Sequence

SEQ ID NO: 17 - ACGACCATGCCGCTGTTCGCCGAC

>Mb1654c
GTGCCAGAGGTCACCCGTGAAGAACCGGCAATCGATGGATGGTTCACCACCGATAAGGCC
GGCAACCCGCATCTGCTCGGCGGCAAGTGTCCCCAGTGCGGCACGTACGTCTTCCCACCC
CGGGCGGACAATTGTCCGAATCCGGCTTGCGGCAGCGACACACTAGAGTCGGTCGGACTG
TCGACCCGCGGAAAGCTTTGGAGCTACACCGAAAACCGGTACGCCCCGCCACCGCCGTAC
CCGGCACCCGACCCCTTTGAGCCGTTTGCCGTGGCCGCGGTGGAACTGGCCGACGAGGGA
CTGATCGTGCTGGGCAAAGTGGTCGATGGCACGCTGGCCGCCGATCTGAAGGTCGGCATG
GAGATGGAGCTGACGACCATGCCGCTGTTCGCCGACGACGACGGTGTGCAGCGCATCGTC
TACGCGTGGCGGATCCCATCGCGCGCCGGCGACGATGCAGAGCGCAGCGATGCTGAGGAG
CGGCGCCGATGA (SEQ ID NO: 19)

Fig. 10E

Protein Sequence

SEQ ID NO: 22 – VLVALAALGTQPWQDFAEQETAGLAIILDNVTHGEWASTILAAGAVV
>Mb2347c
MPTTSMSLRELMLRRRPVSGAPVASGASGNLKRSFGTFQLTMFGVGATIGTGIFFVLAQAVPEAGPGVIVSFIIAGIA
AGLAAICYAELASAVPISGSAYSYAYTTLGEAVAMVVAACLLLEYGVATAAVAVGWSGYVNKLLSNLFGFQMPHVLS
AAPWDTHPGWVNLPAVILIGLCALLLIRGASESARVNAIMVLIKLGVLGMFMIIAFSAYSADHLKDFVPFGVAGIGSAA
GTIFFSYIGLDAVSTAGDEVKDPQKTMPRALIAALVVVTGVY<u>VLVALAALGTQPWQDFAEQETAGLAIILDNVTHG
EWASTILAAGAVV</u>SIFTVTLVTMYGQTRILFAMGRDGLLPARFAKVNPRTMTPVHNTVIVAIFASTLAAFIPLDSLAD
MVSIGTLTAFSVVAVGVIVLRVREPDLPRGFKVPGYPVTPVLSVLACGYILASLHWYTWLAFSGWVAVAVIFYLMWG
RHHSALNEEVP (SEQ ID NO: 24)

DNA Sequence

SEQ ID NO: 21 -
GTGCTGGTCGCACTGGCCGCGCTGGGCACCCAACCGTGGCAGGACTTCGCAGAGCAGGAAACCGCCGGGC
TGGCCATCATCTTGGACAACGTCACGCATGGCGAATGGGCCAGCACGATTCTGGCCGCCGGTGCGGTGGTC
>Mb2347c
TTGCCGACAACGTCGATGAGCCTTCGAGAACTGATGCTGCGGCGCCGCCCGGTGAGCGGCGCCCCGGTCGC
ATCCGGGGCATCGGGGAACCTCAAGCGGAGTTTCGGCACCTTCCAGCTGACCATGTTCGGGGTTGGCGCGA
CGATAGGTACCGGCATCTTTTTCGTGCTTGCCCAGGCAGTTCCAGAGGCCGGCCCGGGCGTGATTGTTTCGT
TCATCATCGCCGGCATCGCCGCTGGGCTCGCGGCTATCTGCTACGCGGAACTGGCTTCCGCCGTGCCGATTT
CCGGGTCGGCGTACTCCTACGCGTACACGACGCTGGGCGAGGCGGTCGCGATGGTGGTGGCGGCCTGCCT
ACTGCTGGAATACGGGGTAGCCACCGCAGCGGTCGCGGTCGGCTGGAGTGGCTACGTGAACAAGCTGCTGA
GTAATCTGTTCGGATTTCAGATGCCGCACGTATTGTCGGCGGCGCCGTGGGACACCCATCCCGGTTGGGTGA
ACCTGCCCGCCGTCATCCTGATCGGGCTATGCGCGCTGCTGTTGATTCGAGGGGCCAGCGAGTCGGCGAGG
GTCAACGCGATCATGGTGCTGATCAAGCTCGGCGTGCTGGGCATGTTCATGATCATCGCGTTCAGCGCGTAC
AGCGCCGACCACCTCAAGGATTTCGTCCCATTCGGCGTCGCCGGCATCGGCTCCGCGGCGGGCACGATCTT
CTTCTCATACATCGGCCTTGACGCGGTGTCGACCGCCGGCGACGAGGTGAAGGACCCGCAGAAGACCATGC
CGCGTGCGCTGATCGCAGCGCTGGTGGTCGTCACCGGTGTCTAC<u>GTGCTGGTCGCACTGGCCGCGCTGGGC
ACCCAACCGTGGCAGGACTTCGCAGAGCAGGAAACCGCCGGGCTGGCCATCATCTTGGACAACGTCACGCA
TGGCGAATGGGCCAGCACGATTCTGGCCGCCGGTGCGGTGGTC</u>TCGATTTTCACCGTCACGCTGGTCACCAT
GTACGGCCAGACCCGGATCCTGTTCGCGATGGGGCGCGACGGGCTGCTGCCGGCGCGGTTCGCGAAGGTG
AATCCGCGCACCATGACGCCGGTGCACAACACGGTGATCGTCGCGATCTTCGCATCGACGCTGGCCGCCTTC
ATACCGCTGGATAGCTTGGCGGACATGGTGTCCATCGGCACGCTCACCGCGTTCAGCGTGGTGGCTGTGGGT
GTGATCGTTCTACGGGTGCGCGAGCCCGACTTACCCCGAGGGTTCAAGGTACCCGGTTACCCTGTGACGCCT
GTTCTTTCGGTGCTGGCCTGCGGGTATATCCTGGCCAGCTTGCACTGGTACACCTGGCTGGCGTTCAGCGGA
TGGGTGGCGGTGGCAGTGATCTTTTACCTGATGTGGGGTCGGCACCACAGTGCGCTCAACGAGGAAGTGCC
GTGA (SEQ ID NO: 23)

Fig. 10F

Protein Sequence

SEQ ID NO: 26 - CAVVLATMPPLLSAIANA

>MT1515
MTLTACEVTAAEAPFDRVSKTIPHPLSWGAALWSVVSVRWATVALLLFLAGLVAQLNGAPEAMWWTLYLACYLAG
GWGSAWAGAQALRNKALDVDLLMIAAAVGAVAIGQIFDGALLIVIFATSGALDDIATRHTAESVKGLLDLAPDQAVVV
QGDGSERVVAASELVVGDRVVVRPGDRIPADGAVLSGASDVDQRSITGESMPVAKARGDEVFAGTVNGSGVLHL
VVTRDPSQTVVARIVELVADASATKAKTQLFIEKIEQRYSLGMVAATLALIVIPLMFGADLRPVLLRAMTFMIVASP<u>CA
VVLATMPPLLSAIANA</u>GRHGVLVKSAVVVERLADTSIVALDKTGTLTRGIPRLASVAPLDPNVVDARRLLQLAA
AAEQSSEHPLGRAIVAEARRRGIAIPPAKDFRAVPGCGVHALVGNDFVEIASPQSYRGAPLAELAPLLSAGATAAIVL
LDGVAIGVLGLTDQLRPDAVESVAAMAALTAAPPVLLTGDNGRAAWRVARNAGITDVRAALLPEQKVEVVRNLQAG
GHQVLLVGDGVNDAPAMAAARAAVAMGAGADLTLQTADGVTIRDELHTIPTIIGLARQARRVVTVNLAIAATFIAVLV
LWDLFGQLPLPLGVVGHEGSTVLVALNGMRLLTNRSWRAAASAAR (SEQ ID NO: 28)

DNA Sequence

SEQ ID NO: 25 - TGCGCGGTGGTGCTGGCCACCATGCCGCCGCTGCTTTCGGCGATCGCC
AACGCA

>MT1515
ATGACCTTGACCGCTTGTGAAGTAACTGCCGCGGAGGCTCCTTTCGACCGCGTTTCAAAGACCATTCCCCACC
CATTGAGCTGGGGAGCCGCGCTGTGGTCGGTAGTCTCCGTGCGCTGGGCCACCGTGGCGCTGCTGCTGTTT
CTCGCCGGACTAGTGGCGCAACTGAACGGTGCTCCCGAGGCCATGTGGTGGACGCTTTACCTGGCCTGTTAT
CTGGCCGGCGGCTGGGGCTCGGCATGGGCGGGCGCACAAGCGTTGCGGAACAAGGCACTTGATGTGGATCT
GCTGATGATTGCCGCGGCGGTCGGAGCGGTCGCGATTGGGCAGATCTTCGACGGCGCGCTGCTGATCGTGA
TCTTCGCCACGTCCGGTGCGCTGGATGACATTGCCACCAGACACACCGCGGAATCGGTCAAAGGCCTGCTGG
ACCTCGCGCCGGATCAGGCGGTGGTGGTCCAGGGCGACGGCAGCGAACGGGTGGTGGCGGCCAGCGAGCT
GGTGGTGGGGGACCGGGTGGTGGTGCGGCCGGGGGACCGGATACCCGCAGACGGCGGTGCTGTCGGG
GGCTAGCGACGTCGACCAACGCTCGATCACCGGTGAATCGATGCCGGTGGCCAAGGCCCGCGGTGACGAGG
TGTTCGCCGGCACCGTGAACGGATCGGGTGTATTGCATCTGGTGGTCACCCGTGACCCGAGCCAGACCGTG
GTAGCCCGCATCGTCGAACTGGTCGCCGACGCTTCGGCGACGAAGGCCAAAACCCAACTGTTCATTGAGAAA
ATCGAGCAACGCTACTCCCTGGGCATGGTCGCGGCCACCCTTGCCCTCATCGTTATTCCGCTGATGTTCGGC
GCCGACCTGCGGCCGGTGCTGCTGCGCGCCATGACCTTCATGATCGTGGCATCGCC<u>ATGCGCGGTGGTGCT
GGCCACCATGCCGCCGCTGCTTTCGGCGATCGCCAACGCA</u>GGCCGTCATGGGGTGCTGGTCAAATCCGCGG
TGGTCGTCGAACGCCTGGCCGATACCAGCATCGTCGCTTTGGACAAGACCGGTACGCTGACCCGTGGCATCC
CGCGACTGGCTTCCGTCGCACCGCTGGACCCCAACGTGGTCGATGCCCGGCGATTGTTGCAATTGGCAGCT
GCCGCAGAACAATCCAGCGAGCACCCGCTTGGCCGGGCGATCGTCGCGGAAGCTCGTCGGCGTGGTATCGC
CATACCGCCCCGCCAAGGACTTCCGCGCGGTCCCGGGCTGCGGGGTCCACGCCCTGGTGGGCAACGATTTCG
TCGAGATCGCCAGCCCGCAAAGCTACCGCGGTGCACCGCTAGCAGAGCTGGCGCCGCTCCTTTCTGCCGGC
GCCACTGCCGCCATCGTCTTGTTGGATGGAGTTGCCATCGGTGTGCTCGGGCTCACCGATCAGCTTCGTCCG
GATGCCGTGGAGTCCGTCGCGGCGATGGCTGCATTGACCGCCGCACCACCGGTGCTGCTCACGGGTGACAA
CGGGCGAGCGGCTTGGCGGGTCGCTCGGAACGCCGGGATCACCGATGTGCGAGCCGCATTGCTGCCCGAG
CAGAAGGTTGAAGTCGTGCGCAACCTGCAGGCCGGTGGTCACCAGGTGCTGCTCGTCGGCGACGGCGTCAA
CGACGCTCCCGCCATGGCCGCCGCCCGCGCCGCTGTCGCCATGGGCGCCGGCGCCGATCTGACCCTACAG
ACCGCAGACGGGGTGACCATACGGGACGAACTGCACACCATCCCGACGATCATCGGGTTGGCACGGCAGGC
GCGCCGGGTGGTCACCGTCAACCTGGCCATCGCGGCCACCTTCATCGCCGTCCTGGTGCTGTGGGACCTTTT
TGGGCAGCTGCCGCTGCCACTGGGTGTGGTGGGTCACGAAGGGTCCACTGTGCTGGTGGCCCTCAACGGCA
TGCGGCTATTGACCAACCGGTCGTGGCGGGCCGCGGCTTCGGCTGCGCGTTAG (SEQ ID NO: 27)

Fig. 10G

| SEQ ID NO: | Sequence | TIGR annotation | Swiss-Prot | Protein Name |
|---|---|---|---|---|
| 2 | DGYVGAPAH (9mer) | MT0401 | P95197 | 5'-PHOSPHORIBOSYLGLYCINAMIDE TRANSFORMYLASE 2 |
| 6 | LAAVVGVVLAQVL (13mer) | Mb0073 | Q7U2X1 | PROBABLE GLUTAMINE-TRANSPORT TRANSMEMBRANE PROTEIN ABC TRANSPORTER |
| 10 | RSGAATPVR (9mer) | MT2160.1 | Q8VJQ5 | HYPOTHETICAL PROTEIN |
| 14 | TCLPFAL (7mer) | MT0910.2 | Q8VKC1 | HYPOTHETICAL PROTEIN |
| 18 | TTMPLFAD (8mer) | Mb1654c | Q7TZV3 | HYPOTHETICAL PROTEIN |
| 22 | VLVALAALGTQPWQDFAEQETAGLAIILDNV THGEWASTILAAGAVV (47mer) | Mb2347c | Q7TYU0 | PROBABLE CATIONIC AMINO ACID TRANSPORT INTEGRAL MEMBRANE PROTEIN ROCE |
| 26 | CAVVLATMPPLLSAIANA (8mer) | Mb1504 | O53160 | PROBABLE CATION-TRANSPORTING P-TYPE ATPASE D |

Fig. 10H

Protein and DNA sequences of TB peptide found in urine of TB patient:

Protein Sequence

SEQ ID NO: 30 - MVIIELMRR

>MT1721
MVIIELMRRVVGLAQGATAEVAVYGDRDRDLAERWCANTGNTLVRADVDQTGVGTLVVRR
GHPPDPASVLGPDRLPGVRLWLYTNFHCNLCCDYCCVSSSPSTPHRELGAERIGRIVGEA
ARWGVRELFLTGGEPFLLPDIDTIIATCVKQLPTTVLTNGMVFKGRGRRALESLPRGLAL
QISLDSATPELHDAHRGAGTWVKAVAGIRLALSLGFRVRVAATVASPAPGELTAFHDFLD
GLGIAPGDQLVRPIALEGAASQGVALTRESLVPEVTVTADGVYWHPVAATDERALVTRTV
EPLTPALDMVSRLFAEQWTRAAEEAALFPCA (SEQ ID NO: 32)

DNA Sequence

SEQ ID NO: 29 - ATGGTGATCATAGAGCTGATGCGCCGG

>MT1721
ATGGTGATCATAGAGCTGATGCGCCGGGTGGTAGGTCTCGCACAGGGAGCTACCGCCGAG
GTCGCCGTCTATGGCGACCGAGATCGTGATCTCGCGGAGCGATGGTGCGCGAACACCGGA
AACACCCTGGTGCGCGCCGACGTGGACCAGACCGGCGTCGGCACCCTGGTGGTGCGCCGC
GGCCATCCGCCTGACCCGGCAAGCGTGTTGGGCCCCGACCGGCTACCCGGGGTCCGGTTG
TGGCTGTACACCAACTTCCACTGCAACCTGTGCTGCGACTACTGCTGCGTCTCGTCGTCA
CCAAGCACCCCGCATCGCGAACTGGGGCGGAGCGGATCGGCCGAATCGTCGGTGAAGCG
GCGCGCTGGGGAGTGCGCGAACTGTTCCTCACCGGCGGTGAGCCGTTCCTGCTGCCCGAC
ATCGACACGATCATCGCGACCTGTGTGAAGCAGTTGCCCACCACCGTCCTCACCAACGGC
ATGGTGTTCAAAGGGCGGGTCGGCGCGCTGGAATCCCTACCTAGAGGGCTCGCCTTG
CAGATCAGCCTGGACTCGGCCACCCCGGAGCTGCACGATGCGCACCGCGGCGCGGGGACG
TGGGTCAAGGCAGTAGCTGGTATCCGGTTGGCGCTCTCACTTGGCTTCCGGGTGCGGGTG
GCCGCGACGGTTGCCAGCCCCGCACCTGGCGAGCTGACGGCGTTTCACGACTTCCTCGAC
GGGCTTGGCATCGCACCCGGGGATCAGCTGGTCCGGCCGATCGCGCTGGAGGGCGCCGCG
TCGCAAGGGGTGGCGCTCACCCGCGAATCGCTGGTTCCCGAGGTGACCGTCACCGCCGAC
GGCGTGTACTGGCACCCAGTGGCCGCCACCGACGAGCGCGCCCTGGTCACCCGTACCGTC
GAACCCTTGACCCCGGCGCTGGACATGGTAAGCCGGCTATTCGCCGAACAGTGGACACGA
GCCGCCGAAGAGGCCGCGTTGTTCCCGTGTGCGTAG (SEQ ID NO: 31)

Fig. 11

*Mycobacterium tuberculosis* peptides found in the urine of patients with pulmonary tuberculosis

| SEQ ID NO: | Peptide | *M. tuberculosis* donor protein |
| --- | --- | --- |
| 34 | RATADQIGTQTTQIAAIKA | Homoserine O-acetyltransferase |
| 38 | RTAEERANAVRGRADSLRR | Chromosome partition protein smc |
| 42 | RLHAQKALLVWLLERS | Ornithine carbamoyltransferase |
| 46 | RWTDETFGDIGGAGGGVSGHRG | Phosphoadenosine phosphosulfate reductase |

Fig. 12

Protein: Homoserine O-acetyltransferase

Peptide: RATADQIGTQTTQIAAIKA (SEQ ID NO: 34)

| TIGR Annotation for MT3444 ||
|---:|:---|
| TIGR Locus Name: | MT3444 |
| Primary Locus Name: | None |
| SWISS-PROT/TrEMBL AC: | O53391 |
| Putative identification: | homoserine O-acetyltransferase |
| Gene Symbol: | metA |
| TIGR Cellular role(s): | Amino acid biosynthesis: Aspartate family |
| Coordinates: | 3725096 to 3726235 |
| DNA Molecule Name: | chromosome Mycobacterium tuberculosis CDC1551 |
| Gene length: | 1140 |
| Protein length: | 379 |
| Molecular Weight: | 39798.68 |
| pI: | 5.3912 |
| Percent GC: | 69.31% |
| Enzyme Commission #: | 2.3.1.31 |
| Kingdom: | Bacteria |
| Family: | Actinobacteria |

Fig. 13A

Protein Sequence

SEQ ID NO: 34 - RATADQIGTQTTQIAAIKA

>MT3444
MTISDVPTQTLPAEGEIGLIDVGSLQLESGAVIDDVCIAVQRWGKLSPARDNVVVLHAL
TGDSHITGPAGPGHPTPGWWDGVAGPSAPIDTTRWCAVATNVLGGCRGSTGPSSLARDGK
PWGSRFPLISIRDQVQADVAALAALGITEVAAVVGGSMGGARALEWVVGYPDRVRAGLLL
AVGARATADQIGTQTTQIAAIKADPDWQSGDYHETGRAPDAGLRLARRFAHLTYRGEIEL
DTRFANHNQGNEDPTAGGRYAVQSYLEHQGDKLLSRFDAGSYVILTEALNSHDVGRGRGG
VSAALRACPVPVVVGGITSDRLYPLRLQQELADLLPGCAGLRVVESVYGHDGFLVETEAV
GELIRQTLGLADREGACRR (SEQ ID NO: 36)

DNA Sequence

SEQ ID NO: 33 - CGTGCCACCGCAGACCAGATCGGCACGCAGACAACGCAAATCGCGGCCATCAAAGCC

>MT3444
ATGACGATCTCCGATGTACCCACCCAGACGCTGCCCGCCGAAGGCGAAATCGGCCTGATA
GACGTCGGCTCGCTGCAACTGGAAAGCGGGGCGGTGATCGACGATGTCTGTATCGCCGTG
CAACGCTGGGGCAAATTGTCGCCCGCACGGGACAACGTGGTGGTGGTCTTGCACGCGCTC
ACCGGCGACTCGCACATCACTGGACCCGCCGGACCCGGCCACCCCACCCCCGGCTGGTGG
GACGGGGTGGCCGGGCCGAGTGCGCCGATTGACACCACCCGCTGGTGCGCGGTAGCTACC
AATGTGCTCGGCGGCTGCCGCGGCTCCACCGGGCCCAGCTCGCTTGCCCGCGACGGAAAG
CCTTGGGGCTCAAGATTTCCGCTGATCTCGATACGTGACCAGGTGCAGGCGGACGTCGCG
GCGCTGGCCGCGCTGGGCATCACCGAGGTCGCCGCCGTCGTCGGCGGCTCCATGGGCGGC
GCCCGGGCCCTGGAATGGGTGGTCGGCTACCCGGATCGGGTCCGAGCCGGATTGCTGCTG
GCGGTCGGTGCGCGTGCCACCGCAGACCAGATCGGCACGCAGACAACGCAAATCGCGGCCATCAAAGCCGACCCGGACTGGCAGAGCGGCGACTACCACGAGACGGGGAGGGCACCAGAC
GCCGGGCTGCGACTCGCCCGCCGCTTCGCGCACCTCACCTACCGCGGCGAGATCGAGCTC
GACACCCGGTTCGCCAACCACAACCAGGGCAACGAGGATCCGACGGCCGGCGGGCGCTAC
GCGGTGCAAAGTTATCTGGAACACCAAGGAGACAAACTGTTATCCCGGTTCGACGCCGGC
AGCTACGTGATTCTCACCGAGGCGCTCAACAGCCACGACGTCGGCCGCGGCCGCGGCGGG
GTCTCCGCGGCTCTGCGCGCCTGCCCGGTGCCGGTGGTGGTGGGCGGCATCACCTCCGAC
CGGCTCTACCCGCTGCGCCTGCAGCAGGAGCTGGCCGACCTGCTGCCGGGCTGCGCCGGG
CTGCGAGTCGTCGAGTCGGTCTACGGACACGACGGCTTCCTGGTGGAAACCGAGGCCGTG
GGCGAATTGATCCGCCAGACACTGGGATTGGCTGATCGTGAAGGCGCGTGTCGGCGGTGA
(SEQ ID NO: 35)

Fig. 13B

Protein: Chromosome partition protein smc

Peptide: RTAEERANAVRGRADSLRR (SEQ ID NO: 38)

| TIGR Annotation for MT2990 ||
|---:|:---|
| TIGR Locus Name: | MT2990 |
| Primary Locus Name: | None |
| SWISS-PROT/TrEMBL AC: | Q10970 |
| Putative identification: | chromosome segregation SMC protein, putative |
| TIGR Cellular role(s): | Cellular processes: Cell division |
| Coordinates: | 3232127 to 3228510 |
| DNA Molecule Name: | chromosome Mycobacterium tuberculosis CDC1551 |
| Gene length: | 3618 |
| Protein length: | 1205 |
| Molecular Weight: | 130637.03 |
| pI: | 4.9064 |
| Percent GC: | 67.28% |
| Kingdom: | Bacteria |
| Family: | Actinobacteria |

FIG. 14A

Protein Sequence

SEQ ID NO: 38 - RTAEERANAVRGRADSLRR

>MT2990
MYLKSLTLKGFKSFAAPTTLRFEPGITAVVGPNGSGKSNVVDALAWVMGEQGAKTLRGGK
MEDVIFAGTSSRAPLGRAEVTVSIDNSDNALPIEYTEVSITRRMFRDGASEYEINGSSCR
LMDVQELLSDSGIGREMHVIVGQGKLEEILQSRPEDRRAFIEEAAGVLKHRKRKEKALRK
LDTMAANLARLTDLTTELRRQLKPLGRQAEAAQRAAAIQADLRDARLRLAADDLVSRRAE
REAVFQAEAAMRREHDEAAARLAVASEELAAHESAVAELSTRAESIQHTWFGLSALAERV
DATVRIASERAHHLDIEPVAVSDTDPRKPEELEAEAQQVAVAEQQLLAELDAARARLDAA
RAELADRERRAAEADRAHLAAVREEADRREGLARLAGQVETMRARVESIDESVARLSERI
EDAAMRAQQTRAEFETVQGRIGELDQGEVGLDEHHERTVAALRLADERVAELQSAERAAE
RQVASLRARIDALAVGLQRKDGAAWLAHNRSGAGLFGSIAQLVKVRSGYEAALAAALGPA
ADALAVDGLTAAGSAVSALKQADGGRAVLVLSDWPAPQAPQSASGEMLPSGAQWALDLVE
SPPQLVGAMIAMLSGVAVVNDLTEAMGLVEIRPELRAVTVDGDLVGAGWVSGGSDRKLST
LEVTSEIDKARSELAAAEALAAQLNAALAGALTEQSARQDAAEQALAALNESDTAISAMY
EQLGRLGQEARAAEEEWNRLLQQRTEQEAVRTQTLDDVIQLETQLRKAQETQRVQVAQPI
DRQAISAAADRARGVEVEARLAVRTAEERANAVRGRADSLRRAAAAEREARVRAQQARAA
RLHAAAVAAAVADCGRLLAGRLHRAVDGASQLRDASAAQRQQRLAAMAAVRDEVNTLSAR
VGELTDSLHRDELANAQAALRIEQLEQMVLEQFGMAPADLITEYGPHVALPPTELEMAEF
EQARERGEQVIAPAPMPFDRVTQERRAKRAERALAELGRVNPLALEEFAALEERYNFLST
QLEDVKAARKDLLGVVADVDARILQVFNDAFVDVEREFRGVFTALFPGGEGRLRLTEPDD
MLTTGIEVEARPPGKKITRLSLLSGGEKALTAVAMLVAIFRARPSPFYIMDEVEAALDDV
NLRRLLSLFEQLREQSQIIIITHQKPTMEVADALYGVTMQNDGITAVISQRMRGQQVDQL
VTNSS (SEQ ID NO: 40)

DNA Sequence

SEQ ID NO: 37 -
**CGCACCGCCGAGGAACGCGCCAACGCGGTTCGCGGGCGGGCCGATTCGCTG
CGCCGT**
>MT2990
GTGTACCTCAAGAGTCTGACGTTGAAGGGCTTCAAGTCCTTCGCCGCGCCGACGACTTTA
CGCTTCGAGCCGGGCATTACGGCCGTCGTTGGGCCCAACGGCTCCGGCAAATCCAATGTG
GTCGATGCCCTGGCGTGGGTGATGGGGGAGCAGGGGGCAAAGACGCTGCGCGGCGGCAAG
ATGGAAGACGTCATCTTCGCCGGCACCTCGTCGCGTGCGCCGCTGGGCCGCGCCGAAGTC
ACCGTTAGCATCGACAACTCCGACAACGCACTGCCTATCGAATACACCGAGGTGTCGATC
ACCCGAAGAATGTTTCGCGACGGTGCCAGCGAATACGAAATCAACGGCAGCAGTTGCCGT
TTGATGGATGTGCAGGAGTTGCTGAGCGACTCCGGCATCGGCCGTGAGATGCATGTGATT
GTTGGGCAAGGGAAGCTCGAGGAGATCTTGCAGTCGCGGCCTGAGGATCGGCGGGCGTTC
ATCGAGGAAGCCGCCGGTGTGCTCAAGCATCGCAAGCGCAAGGAAAAGCTCTGCGCAAA
CTCGACACGATGGCGGCGAACCTGGCCCGGCTCACCGATCTGACCACCGAGCTCCGGCGT
CAACTCAAACCGCTGGGCCGGCAGGCCGAGGCGGCCCAGCGTGCCGCGGCCATCCAAGCC
GATCTGCGCGACGCCCGGCTGCGCCTGGCGGCCGACGACTTGGTAAGCCGCAGAGCCGAA
CGGGAAGCGGTCTTTCAGGCCGAGGCTGCGATGCGCCGCGAGCATGACGAGGCCGCCGCC
CGGCTGGCGGTGGCATCCGAGGAGCTGGCCGCGCATGAGTCCGCGGTCGCCGAACTCTCG
ACGCGGGCCGAGTCGATCCAGCACACTTGGTTCGGGCTGTCTGCGCTGGCCGAACGGGTG
GACGCTACGGTGCGCATCGCCAGCGAACGCGCCCATCATCTCGATATCGAGCCGGTAGCG

FIG. 14B

GTCAGCGACACCGACCCCAGAAAGCCCGAGGAGCTAGAAGCCGAGGCCCAGCAGGTGGCC
GTCGCCGAGCAACAACTGTTAGCGGAGCTGGACGCGGCGCGTGCCCGACTCGATGCTGCC
CGTGCAGAGCTGGCCGACCGGGAGCGCCGCGCCGCCGAGGCCGACCGGGCACACCTGGCG
GCGGTCCGGGAGGAGGCGGACCGCCGTGAGGGACTGGCGCGGCTGGCTGGCCAGGTGGAG
ACCATGCGGGCGCGTGTCGAATCGATCGATGAGAGCGTGGCACGGTTGTCCGAGCGGATC
GAGGATGCCGCAATGCGCGCCCAGCAGACCCGAGCCGAGTTCGAAACCGTGCAGGGCCGC
ATCGGTGAACTGGATCAAGGCGAGGTCGGCCTGGATGAGCACCACGAGCGTACTGTGGCC
GCGTTGCGGTTGGCCGACGAACGCGTCGCCGAGCTGCAATCCGCCGAACGCGCCGCCGAA
CGCCAGGTGGCATCGCTACGGGCTCGCATCGATGCGCTCGCAGTGGGGCTACAGCGCAAG
GACGGCGCGGCGTGGCTGGCGCACAATCGCAGTGGCGCAGGGCTTTTCGGTTCGATCGCC
CAATTGGTGAAGGTACGTTCCGGCTATGAAGCGGCACTGGCCGCGGCGCTCGGGCCGGCG
GCCGACGCACTTGCGGTGGACGGCCTGACTGCCGCGGGTAGTGCCGTCAGCGCACTCAAA
CAAGCCGACGGCGGTCGCGCGGTCCTCGTGCTGAGTGACTGGCCGGCCCCGCAAGCCCCC
CAATCCGCCTCGGGGGAGATGCTGCCTAGCGGCGCCCAGTGGGCCCTAGACCTGGTCGAG
TCTCCACCGCAGTTGGTTGGCGCGATGATCGCCATGCTTTCGGGTGTCGCGGTGGTCAAC
GACCTGACTGAGGCAATGGGCCTGGTCGAGATTCGTCCGGAGCTACGCGCGGTCACCGTT
GACGGTGATCTGGTGGGCGCCGGCTGGGTCAGCGGCGGATCGGACCGCAAGCTGTCCACC
TTGGAGGTCACCTCCGAGATCGACAAGGCCAGGAGTGAGCTGGCCGCTGCCGAGGCGCTG
GCGGCGCAATTGAATGCGGCCCTGGCCGGTGCGCTGACCGAGCAGTCCGCCCGCCAGGAC
GCGGCCGAGCAAGCCTTGGCCGCGCTTAACGAATCCGACACGGCCATCTCGGCGATGTAC
GAGCAGCTGGGCCGCCTCGGGCAGGAGGCCCGCGCGGCGGAAGAAGAGTGGAACCGGTTG
CTGCAGCAGCGTACGGAACAGGAAGCCGTGCGCACACAGACTCTCGACGACGTCATACAA
CTTGAGACCCAGCTGCGTAAGGCCCAGGAGACCCAACGGGTGCAGGTGGCCCAACCGATC
GACCGCCAGGCGATCAGTGCCGCTGCCGATCGCGCCCGCGGTGTCGAAGTGGAAGCCCGG
CTGGCGGTGCGCACCGCCGAGGAACGCGCCAACGCGGTTCGCGGGCGGGCCGATTCGCTG
CGCCGTGCGGCAGCGGCGGAACGTGAGGCGCGGGTGCGGGCTCAGCAAGCACGCGCCGCA
AGACTGCATGCGGCCGCGGTGGCCGCAGCGGTCGCCGACTGCGGACGGCTGCTGGCCGGG
CGGTTGCACCGGGCGGTGGACGGGGCGTCGCAACTGCGCGACGCGTCGGCCGCGCAACGT
CAGCAGCGGTTAGCGGCGATGGCCGCGGTGCGCGACGAGGTGAACACGCTGAGCGCCCGA
GTGGGGGAACTCACCGATTCGCTGCACCGCGACGAGCTGGCTAACGCGCAGGCGGCGCTG
CGTATCGAGCAGCTTGAGCAGATGGTGCTAGAGCAGTTCGGAATGGCGCCGGCCGACTTG
ATCACCGAATACGGTCCACATGTGGCGCTACCACCGACCGAGCTCGAGATGGCTGAGTTC
GAGCAAGCCCGCGAACGCGGCGAGCAGGTGATTGCGCCCGCCCCATGCCGTTCGACCGG
GTTACCCAGGAGCGCCGGGCCAAACGCGCCGAGCGTGCGCTTGCCGAGTTGGGCAGGGTC
AACCCGCTGGCGCTCGAAGAGTTTGCTGCCTTGGAGGAGCGCTACAATTTCCTGTCCACC
CAACTCGAGGATGTCAAGGCTGCCCGCAAGGATCTGCTGGGCGTCGTCGCCGATGTTGAC
GCCCGCATCCTGCAGGTGTTCAATGACGCGTTCGTAGACGTGGAACGCGAATTTCGCGGC
GTGTTCACCGCATTGTTCCCCGGTGGTGAAGGACGGCTGCGGCTGACCGAGCCCGACGAC
ATGCTCACCACCGGCATCGAGGTCGAAGCCCGCCCGCCGGGCAAGAAGATTACCCGACTG
TCTTTGCTCTCCGGTGGCGAGAAGGCGCTGACCGCGGTGGCGATGCTGGTCGCGATCTTT
CGTGCCCGTCCATCGCCGTTCTACATCATGGACGAGGTGGAGGCCGCCCTCGACGACGTG
AACCTGCGCCGACTGCTCAGCCTGTTCGAACAGCTGCGAGAGCAGTCGCAGATCATCATC
ATCACCCACCAGAAGCCGACGATGGAGGTCGCGGACGCACTGTACGGCGTAACCATGCAG
AACGACGGCATCACCGCGGTCATCTCGCAGCGCATGCGCGGTCAGCAGGTGGATCAGCTG
GTTACCAATTCCTCGTAG (SEQ ID NO: 39)

FIG. 14C

Protein: Ornithine carbamoyltransferase

Peptide: RLHAQKALLVWLLERS (SEQ ID NO: 42)

| TIGR Annotation for MT1694 ||
|---:|:---|
| TIGR Locus Name: | MT1694 |
| Primary Locus Name: | None |
| SWISS-PROT/TrEMBL AC: | P94991 |
| Putative identification: | ornithine carbamoyltransferase |
| Gene Symbol: | argF |
| TIGR Cellular role(s): | Amino acid biosynthesis: Glutamate family |
| Coordinates: | 1860829 to 1861752 |
| DNA Molecule Name: | chromosome Mycobacterium tuberculosis CDC1551 |
| Gene length: | 924 |
| Protein length: | 307 |
| Molecular Weight: | 33057.22 |
| pI: | 5.0574 |
| Percent GC: | 68.95% |
| Enzyme Commission #: | 2.1.3.3 |
| Kingdom: | Bacteria |
| Family: | Actinobacteria |

FIG. 15A

Protein Sequence

SEQ ID NO: 42 - RLHAQKALLVWLLERS

>MT1694
MIRHFLRDDDLSPAEQAEVLELAAELKKDPVSRRPLQGPRGVAVIFDKNSTRTRFSFELG
IAQLGGHAVVVDSGSTQLGRDETLQDTAKVLSRYVDAIVWRTFGQERLDAMASVATVPVI
NALSDEFHPCQVLADLQTIAERKGALRGLRLSYFGDGANNMAHSLLLGGVTAGIHVTVAA
PEGFLPDPSVRAAAERRAQDTGASVTVTADAHAAAAGADVLVTDTWTSMGQENDGLDRVK
PFRPFQLNSRLLALADSDAIVLHCLPAHRGDEITDAVMDGPASAVWDEAEN**RLHAQKALL
VWLLERS**  (SEQ ID NO: 44)

DNA Sequence

SEQ ID NO: 41 - CTGCACGCGCAGAAGGCGCTGCTGGTGTGGCTGCTGGAGCGCTCATGA

>MT1694
GTGATCAGGCATTTCCTGCGCGACGACGATCTGTCCCCGGCCGAACAGGCCGAGGTGCTC
GAGCTCGCGGCCGAGCTGAAGAAAGACCCGGTTAGCCGTCGTCCCTGCAAGGGCCGCGC
GGGGTGGCGGTCATCTTCGACAAGAACTCCACCCGCACCCGGTTCTCCTTCGAGCTGGGC
ATCGCGCAGCTGGGCGGGCATGCCGTCGTCGTCGACAGCGGCAGCACCCAGCTGGGCCGC
GACGAAACCCTGCAGGACACCGCAAAGGTGTTGTCCCGCTACGTCGATGCCATCGTCTGG
CGAACCTTCGGCCAAGAGCGGCTGGACGCCATGGCGTCGGTCGCGACGGTGCCCGTGATC
AACGCGCTCTCCGATGAGTTCCATCCGTGTCAGGTGTTGGCCGACCTGCAGACCATCGCC
GAACGCAAGGGGGCGCTGCGCGGCCTGAGGTTGTCCTACTTCGGCGACGGCGCCAACAAC
ATGGCCCACTCGCTGCTGCTCGGCGGGGTCACCGCGGGTATCCACGTCACCGTCGCGGCT
CCCGAGGGCTTCCTGCCCGACCCGTCGGTGCGGGCCGCGGCCGAGCGCCGCGCCCAGGAT
ACCGGCGCCTCGGTGACTGTGACCGCCGACGCCCACGCGGCCGCCGCCGGCGCCGACGTT
CTGGTCACCGACACCTGGACGTCGATGGGCCAGGAAAACGACGGGTTGGACCGAGTGAAG
CCGTTTCGGCCGTTTCAGCTCAACTCGCGACTTCTGGCGCTGGCCGACTCGGATGCCATC
GTGTTGCATTGCCTGCCGGCCCATCGCGGCGACGAGATCACCGACGCGGTGATGGACGGG
CCGGCCAGCGCGGTGTGGGACGAGGCCGAAAACCGG**CTGCACGCGCAGAAGGCGCTGCTG
GTGTGGCTGCTGGAGCGCTCATGA**  (SEQ ID NO: 43)

FIG. 15B

Protein: Probable phosphoadenosine phosphosulfate reductase

Peptide: RWTDETFGDIGGAGGGVSGHRG (SEQ ID NO: 46)

| TIGR Annotation for MT2462 ||
|---:|:---|
| TIGR Locus Name: | MT2462 |
| Primary Locus Name: | None |
| SWISS-PROT/TrEMBL AC: | P71752 |
| Putative identification: | phosphoadenosine phosphosulfate reductase |
| Gene Symbol: | cysH |
| TIGR Cellular role(s): | Amino acid biosynthesis: Serine family<br>Central intermediary metabolism: Sulfur metabolism |
| Coordinates: | 2683698 to 2684462 |
| DNA Molecule Name: | chromosome Mycobacterium tuberculosis CDC1551 |
| Gene length: | 765 |
| Protein length: | 254 |
| Molecular Weight: | 27422.87 |
| pI: | 4.9994 |
| Percent GC: | 64.30% |
| Enzyme Commission #: | 1.8.99.4 |
| Kingdom: | Bacteria |
| Family: | Actinobacteria |

FIG. 16A

Protein Sequence

SEQ ID NO: 46 - RWTDETFGDIGGAGGGVSGHRG

>MT2462
MSGETTRLTEPQLRELAARGAAELDGATATDMLRWTDETFGDIGGAGGGVSGHRGWTTCN
YVVASNMADAVLVDLAAKVRPGVPVIFLDTGYHFVETIGTRDAIESVYDVRVLNVTPEHT
VAEQDELLGKDLFARNPHECCRLRKVVPLGKTLRGYSAWVTGLRRVDAPTRANAPLVSFD
ETFKLVKVNPLAAWTDQDVQEYIADNDVLVNPLVREGYPSIGCAPCTAKPAEGADPRSGR
WQGLAKTECGLHAS (SEQ ID NO: 48)

DNA Sequence

SEQ ID NO: 45 - **CGCTGGACCGACGAAACCTTCGGCGACATCGGCGGCGCC
GGCGGCGGCGTGAGCGGACATCGCGGG**

>MT2462
ATGAGCGGCGAGACAACCAGGCTGACCGAACCGCAACTACGTGAGCTGGCCGCGCGCGGA
GCTGCCGAACTCGACGGCGCCACCGCCACCGACATGTTG**CGCTGGACCGACGAAACCTTC
GGCGACATCGGCGGCGCCGGCGGCGGCGTGAGCGGACATCGCGGG**TGGACAACGTGCAAC
TACGTAGTTGCTTCCAACATGGCTGATGCGGTGCTGGTGGATCTGGCCGCCAAGGTGCGA
CCGGGCGTACCGGTCATCTTTCTTGATACCGGCTACCACTTCGTCGAAACAATCGGCACC
AGAGATGCGATCGAGTCCGTCTATGACGTCCGGGTGCTCAATGTCACTCCGGAGCACACA
GTGGCCGAGCAGGACGAACTGCTGGGCAAGGACTTGTTCGCCCGCAACCCCCATGAATGC
TGCCGGTTGCGCAAGGTCGTTCCCCTGGGCAAGACGCTGCGTGGCTACTCCGCGTGGGTG
ACCGGGCTACGGCGGGTCGATGCACCGACCCGGGCCAATGCCCCGCTGGTCAGCTTCGAT
GAGACGTTCAAACTAGTGAAGGTCAACCCGCTGGCGGCGTGGACCGACCAAGATGTGCAG
GAATACATTGCCGACAACGACGTGCTGGTTAATCCGCTTGTGCGGGAAGGCTATCCGTCG
ATCGGTTGCGCTCCGTGCACAGCCAAACCCGCCGAAGGCGCCGACCCGCGCAGCGGACGC
TGGCAGGGGCTGGCCAAGACCGAATGCGGGTTGCACGCCTCGTGA (SEQ ID NO:47)

FIG. 16B

The following is the nucleotide sequence of 85b antigen fused to the pulA signal peptide.

```
   1 ATGGTCTACA GCATCCGTTC CCTCAAAAAT GGAACTGGTT CTGTCCTTAT
  51 TGGAGCAAGC CTTATTCTGC TTGCCATGGC TACACCAACT ATCTCAGCAA
 101 ACGAAAATAC ACCAACCACT AACGAACCCA GCAACAGAAA TACGACCTCC
 151 CTTACTCAAC CTCTTACTGA TGCAACAAAC ATCGCTGGCA AGAACGAAAG
 201 CGATTTTTCT TCACCCGATA GTGCAAACGC TTCCATGACA GACGTTTCTA
 251 GAAAAATTCG TGCTTGGGGA AGACGTTTAA TGATTGGAAC CGCTGCTGCC
 301 GTTGTTTTAC CTGGACTCGT TGGATTAGCC GGTGGCGCCG CTACAGCCGG
 351 AGCTTTTTCT CGTCCTGGTT TGCCTGTTGA ATATTTACAA GTTCCTTCTC
 401 CATCTATGGG TCGCGATATC AAAGTACAAT TTCAGTCTGG TGGCAATAAC
 451 TCTCCTGCCG TTTACTTACT CGATGGTCTC CGTGCACAAG ACGATTACAA
 501 TGGTTGGGAC ATTAATACTC CTGCATTTGA ATGGTACTAT CAGTCAGGTC
 551 TCTCAATCGT AATGCCTGTC GGTGGTCAAA GTAGTTTTTA TTCTGATTGG
 601 TACTCACCTG CCTGTGGAAA AGCAGGATGT CAAACTTACA AATGGGAAAC
 651 ATTCTTAACT TCAGAGCTTC CACAATGGTT ATCCGCAAAT CGAGCTGTTA
 701 AACCTACTGG GTCTGCTGCT ATTGGTCTAT CTATGGCTGG TTCTTCCGCA
 751 ATGATCTTAG CTGCTTATCA TCCACAACAA TTTATTTATG CTGGCTCACT
 801 ATCTGCTCTT CTAGATCCTT CTCAAGGTAT GGGACCAAGT TTAATTGGAT
 851 TAGCTATGGG CGACGCTGGA GGTTACAAAG CTGCCAATAT GTGGGGACCT
 901 TCTTCTGATC CTGCCTGGGA ACGAAATGAT CCAACACAAC AAATTCCAAA
 951 ATTAGTAGCA AATAACACAC GTTTATGGGT TTACTGTGGT AATGGCACAC
1001 CAAATGAACT TGGAGGGGCT AACATTCCTG CTGAATTCTT AAAAAATTTT
1051 GTTAGAAGCT CAAACTTAAA ATTTCAAGAC GCATATAACG CAGCTGGAGG
1101 GCATAATGCT GTATTTAATT TTCCTCCAAA CGGAACACAT TCATGGGAAT
1151 ATTGGGGCGC ACAATTAAAT GCTATGAAAG GAGATTTACA AAGTTCACTA
1201   TGCTGGTT AA (SEQ ID NO: 53)
```

Fig. 17A

The following is the amino of 85b antigen fused to the pulA signal peptide.

```
        10         20         30         40         50         60
MVYSIRSLKN GTGSVLIGAS LILLAMATPT ISANENTPTT NEPSNRNTTS LTQPLTDATN 70         80         90        100        110        120
IAGKNESDFS SPDSANASNE LFSRPGLPVE YLQVPSPSMG RDIKVQFQSG GNNSPAVYLL 130        140        150        160        170        180
DGLRAQDDYN GWDINTPAFE WYYQSGLSIV MPVGGQSSFY SDWYSPACGK AGCQTYKWET 190        200        210        220        230        240
FLTSELPQWL SANRAVKPTG SAAIGLSMAG SSAMILAAYH PQQFIYAGSL SALLDPSQGM 250        260        270        280        290        300
GPSLIGLAMG DAGGYKAANM WGPSSDPAWE RNDPTQQIPK LVANNTRLWV YCGNGTPNEL 310        320        330        340        350        360
GGANIPAEFL KNFVRSSNLK FQDAYNAAGG HNAVFNFPPN GTHSWEYWGA QLNAMKGDLQ

SSLGAG (SEQ ID NO: 54)
```

Fig. 17B

The nucleotide sequence for pula-HIVgp120 fusion protein:

```
   1  ATGGTCTACA GCATCCGTTC CCTCAAAAAT GGAACTGGTT CTGTCCTTAT
  51  TGGAGCAAGC CTTATTCTGC TTGCCATGGC TACACCAACT ATCTCAGCAA
 101  ACGAAAATAC ACCAACCACT AACGAACCCA GCAACAGAAA TACGACCTCC
 151  CTTACTCAAC CTCTTACTGA TGCAACAAAC ATCGCTGGCA AGAACGAAAG
 201  CGATTTTTCT TCACCCGATA GTGCAAACGC TTCCGCAACT ACAACCCTTT
 251  TTTGCGCTTC AGACGCCAAA GCTTACGATA CTGAAGTCCA TAATGTCTGG
 301  GCTACGCATG CCTGTGTACC TACTGACCCT AACCCACAAG AAGTCGTACT
 351  AGTAAATGTC ACCGAGAATT TCAATATGTG GAAGAATGAT ATGGTGGAGC
 401  AAATGCACGA AGATATCATC AGTTTATGGG ATCAAAGCTT AAAACCTTGT
 451  GTCAAACTCA CCCCATTATG TGTCTCTCTC AAATGCACAG ATCTAAAAAA
 501  CGATACCAAC ACTAACTCAT CATCTGGAAG AATGATTATG GAAAAGGAG
 551  AAATTAAAAA TTGTAGTTTT AACATCAGCA CATCTATTCG CGGTAAAGTA
 601  CAAAAAGAAT ACGCATTTTT TTATAAACTT GATATTATCC CAATCGACAA
 651  TGATACAACT AGTTACTCAC TTACGTCTTG TAATACCTCA GTCATTACCC
 701  AAGCTTGTCC AAAAGTAAGT TTTGAACCAA TTCCAATTCA TTATTGCGCA
 751  CCAGCCGGGT TTGCTATTTT AAAATGTAAT AATAAAACCT TCAATGGCAC
 801  AGGTCCTTGT ACAAATGTTT CAACCGTCCA ATGTACTCAC GGTATTCGTC
 851  CAGTCGTCAG CACACAACTC TTACTTAATG GTAGCTTAGC AGAAGAAGAG
 901  GTCGTCATCA GATCAGTTAA TTTTACAGAC AACGCAAAAA CAATCATCGT
 951  CCAGCTCAAC ACTTCAGTAG AGATTAATTG TACTAGACCT AACAACAACA
1001  CCAGAAAACG AATCCGAATC CAAAGAGGGC AGGACGCGC CTTTGTTACG
1051  ATCGGTAAAA TCGGAAATAT GAGACAAGCT CATTGCAATA TTAGTAGAGC
1101  AAAATGGAAC AATACCCTTA ACAAATCGC TTCTAAGTTA AGAGAACAGT
1151  TTGGTAACAA TAAAACCATT ATTTTTAAAC AATCATCAGG CGGGGATCCA
1201  GAAATCGTAA CTCATTCATT TAATTGCGGA GGAGAATTTT TTTATTGTAA
1251  CTCAACACAA CTATTCAATA GCACTTGGTT TAATTCTACT TGGTCAACAG
1301  AAGGTTCAAA TAATACAGAA GGATCAGATA CAATTACATT ACCATGTCGT
1351  ATTAAGCAAA TTATTAACAT GTGGCAAAAA GTTGGAAAAG CTATGTATGC
1401  TCCTCCTATT TCAGGACAAA TTCGATGCTC TTCAAATATC ACAGGACTTT
1451  TATTAACTAG AGATGGAGGG AATTCAAATA ACGAAAGCGA GATTTTCAGA
1501  CCAGGCGGAG GAGATATGAG AGATAACTGG CGCAGTGAAT TATATAAATA
1551  CAAAGTTGTT AAAATCGAAC CATTAGGAGT AGCCCCAACC AAAGCAAAAC
1601  GTCGCGTTGT CCAATCAGAA AAGTCAGCCG TATTAGAACA ATTAGAATCA
1651  ATCATTAATT TGAAAAACT CACAGAATGG ACCAGCTTTC TAGAACATCA
1701  TCATCATCAC CATTAA (SEQ ID NO: 51)
```

Fig. 17C

The amino acid for pula-HIVgp120 fusion protein:

```
        10         20         30         40         50         60
MVYSIRSLKN GTGSVLIGAS LILLAMATPT ISANENTPTT NEPSNRNTTS LTQPLTDATN 70         80         90        100        110        120
IAGKNESDFS SPDSANASAT TTLFCASDAK AYDTEVHNVW ATHACVPTDP NPQEVVLVNV 130        140        150        160        170        180
TENFNMWKND MVEQMHEDII SLWDQSLKPC VKLTPLCVSL KCTDLKNDTN TNSSSGRMIM 190        200        210        220        230        240
EKGEIKNCSF NISTSIRGKV QKEYAFFYKL DIIPIDNDTT SYSLTSCNTS VITQACPKVS 250        260        270        280        290        300
FEPIPIHYCA PAGFAILKCN NKTFNGTGPC TNVSTVQCTH GIRPVVSTQL LLNGSLAEEE 310        320        330        340        350        360
VVIRSVNFTD NAKTIIVQLN TSVEINCTRP NNNTRKRIRI QRGPGRAFVT IGKIGNMRQA 370        380        390        400        410        420
HCNISRAKWN NTLKQIASKL REQFGNNKTI IFKQSSGGDP EIVTHSFNCG GEFFYCNSTQ 430        440        450        460        470        480
LFNSTWFNST WSTEGSNNTE GSDTITLPCR IKQIINMWQK VGKAMYAPPI SGQIRCSSNI 490        500        510        520        530        540
TGLLLTRDGG NSNNESEIFR PGGGDMRDNW RSELYKYKVV KIEPLGVAPT KAKRRVVQSE 550        560        570
KSAVLEQLES IINFEKLTEW TSFLEHHHHH H (SEQ ID NO: 52)
```

Fig. 17D

The nucleotide sequence for the HIV T20 36-amino acid peptide

TATACATCACTCATTCACTCACTCATCGAAGAATCACAAAATCAGCAGGAAAAAAACGAACAAGAATTATTAG
AATTAGACAAATGGGCATCACTTTGGAATTGGTTT  SEQ ID NO: 49)

HIV T20 36-amino acid peptide:
YTSLIHSLIEESQNQQEKNEQELLELDKWASLWNWF (SEQ ID NO: 50)

Fig. 17E

VACCINE AND THERAPEUTIC DELIVERY SYSTEM

RELATED APPLICATIONS

This application claims the benefit of U.S. Provisional Application No. 61/538,346 Sep. 23, 2011, entitled, "Mucosal Vaccination Against Infectious Diseases Delivered By Abundant Commensal Oral Bacteria" by Campos-Neto, Antonio et al.

The entire teachings of the above application are incorporated herein by reference.

GOVERNMENT SUPPORT

The invention was supported, in whole or in part, by a grant R01AI076425 from National Institutes of Health-National Institute of Allergy and Infectious Disease and by a grant R01DE015931 from National Institutes of Health, National Institute of Dental and Craniofacial Research. The Government has certain rights in the invention.

BACKGROUND OF THE INVENTION

Most immunization strategies of current vaccines use protocols that prime and boost the immune system using a parenteral route e.g., intra-dermal, sub-cutaneous and intra-muscular. These means of immunization generate strong systemic immunity but little or no mucosal immunity. In addition, this traditional vaccination protocol, despite inducing both long-lived central memory T cells and short-lived effector T cells, does not sustain a reasonable pool of the latter. These cells, which express CD4 surface antigen and recognize antigenic peptides displayed on the surface of MHC II molecules are the main orchestrators of the immune response. The short-lived T helper cells influence the function of important effector cells including CD8 cytotoxic T cells, antibody producing B lymphocytes and macrophages all of which are important in generation of a successful immune response and subsequent memory.

The primary reason for using a mucosal route of vaccination is that most infections affect or start from a mucosal surface and that in these infections, topical application of a vaccine is often required to induce a protective immune response. Examples include gastrointestinal infections caused by *Helicobacter pylori*, *Vibrio cholera*; enterotoxigenic infections caused by *Escherichia coli*; respiratory infections caused by *Mycobacterium tuberculosis* and *Mycoplasma pneumonia*; and sexually transmitted genital infections caused by HIV, herpes simplex virus, and *Chlamydia trachomatis*.

Therefore, a need exists for a vaccination method in which mucosal immunity is provided. Yet a further need exists for using persistent and abundant commensal oral organisms to deliver antigens for mucosal immunization against infectious diseases. Yet a further need exists for a vaccination protocol that provides generation and maintenance of a significant pool of protective effector and memory T cells.

SUMMARY OF THE INVENTION

The present invention relates to integrally transformed non-pathogenic, commensal bacterium that can express one or more nucleic acid molecules of one or more foreign polypeptides therein. The nucleic acid molecule that encodes the foreign polypeptide is stably integrated into genomic DNA of the bacterium. The commensal bacterium used in the present invention includes e.g., one or more of the following: *Streptococcus mitis*, *Streptococcus oxalis*, *Streptococcus sanguis*, *Streptococcus salivarius*, *Streptococcus constellatus*, *Lactobacillus casei*, *Lactobacillus fermenti*, *Veillonella parvula*, *Prevotella melaninogenica*, *Eikenella corrodens*, *Neisseria mucosa*, *Actinomyces odontolyticus*, *Fusobacterium periodonticum*, *Borrelia vincentii*, and *Actinomyces naeslundii*. The nucleic acid molecule of the foreign polypeptide includes an antigen that elicits an immunogenic response in the individual, a vaccine antigen, an inhibitor of a pathogen, an immune booster, a modulator, a composition used in the treatment of a disease or condition, or a combination thereof. Examples of vaccine antigens include *Mycobacterium leprae* antigens, *Mycobacterium tuberculosis* antigens, malaria sporozoites and merozoites, diphtheria toxoid, tetanus toxoids, *Leishmania* antigens, *Salmonella* antigens, *Mycobacterium africanum* antigens, *Mycobacterium intracellulare* antigens, *Mycobacterium avium* antigens, *Treponema* antigens, Pertussis antigens, Herpes virus antigens, Measles virus antigens, Mumps virus antigens, *Shigella* antigens, *Neisseria* antigens, *Borrelia* antigens, Rabies virus antigens, polio virus antigens, human immunodeficiency virus antigens, snake venom antigens, insect venom antigens, hepatitis A, B, C virus, human papilloma virus antigens, *Vibrio cholera*, *Candida albicans*, *Candida tropicalis*, *Paracoccidioides brasiliensis*, and the like. Examples of inhibitors of a pathogen are small, antimicrobial peptides (e.g., defensins) that can have an effect against various pathogens, including *M. tuberculosis*, *M. leprae*, *M. africanum*, *M. intracellulare*; *M. avium*; Malaria; Diphtheria; *Leishmania*; *Salmonella*; *Treponema*; Pertussis; Herpes virus; Measles virus; Mumps virus; *Shigella*; *Neisseria*; *Borrelia*; rabies virus; polio virus; Human and human immunodeficiency virus types I and II; Hepatitis A, B, C virus, *Vibrio cholera*, *Candida albicans*, *Candida tropicalis*, and *Paracoccidioides brasiliensis*, etc. Immune boosters and/or modulators include e.g., interleukins, interferons, and cytokines such as IL-1, IL-2, IL-4, IL-6, IL-8, IL-12, IL-17, IL-2 IL-21 and IL-22 and cytokines GMCSF, MCSF, MIP1alpha and beta, TNFalpha and beta, IFNalpha and beta and TGFbeta. Additionally, in an embodiment of the present invention, the nucleic acid molecule of the foreign polypeptide is transformed into a gene that expresses a polypeptide in the cytoplasm, in the cell membrane or cell wall or exports it to the cell surface of the bacterium. In one embodiment, the present invention includes utilizing *S. mitis* as the non-pathogenic, commensal bacterium, and the gene that expresses or secretes a polypeptide on the bacteria's cell surface is the serine-rich GspB homologue, the pullulanase polypeptide, or both. The present invention also embodies a foreign polypeptide that is a HIV vaccine, a tuberculosis vaccine, malaria vaccine, leishmaniasis vaccine, herpes virus vaccine, hepatitis virus vaccine, or a combination thereof. Examples of the HIV antigen that can be used with the present invention are gp120 env, gp140 env, gp160 env, gag, pol, nef, vif, vpr, vpu, tat, rev, nef or HIV T20 polypeptide inhibitor. In a particular embodiment, the present invention includes commensal bacteria that have a nucleic acid sequence that encodes the HIV T20 polypeptide, the nucleic acid sequence is set forth in SEQ ID NO: 49. The present invention also includes a commensal bacterium that encodes a foreign polypeptide that encodes the HIV T20 polypeptide according to SEQ ID NO: 50. The commensal bacterium, in an aspect, has a nucleic acid molecule that encodes HIV T20 and is inserted into a gene that expresses or secretes a pullulanase polypeptide, to thereby obtain a gene that expresses or secretes an HIV gp120/pullulanase fusion protein. The nucleic acid molecule of the HIV gp120/pullulanase fusion protein has a sequence of SEQ ID NO: 51, and encodes a sequence of SEQ ID NO: 52.

In an embodiment, the integrally transformed non-pathogenic, commensal bacterium can encode a *M. tuberculosis* antigen having a polypeptide sequence of an amino acid sequence encoded by a nucleic acid molecule. The nucleic acid molecules can be any one of the following: SEQ ID NO: 1, 3, 5, 7, 9, 11, 13, 15, 17, 19, 21, 23, 25, 27, 29, 31, 33, 35, 37, 39, 41, 43, 45, 47, or combination thereof; an amino acid sequence encoded by a coding region of a nucleic acid molecule of SEQ ID NO: 1, 3, 5, 7, 9, 11, 13, 15, 17, 19, 21, 23, 25, 27, 29, 31, 33, 35, 37, 39, 41, 43, 45, 47, or combination thereof; an amino acid sequence encoded by a complement of SEQ ID NO: 1, 3, 5, 7, 9, 11, 13, 15, 17, 19, 21, 23, 25, 27, 29, 31, 33, 35, 37, 39, 41, 43, 45, 47, or combination thereof; an amino acid sequence encoded by a nucleic acid molecule that hybridizes to SEQ ID NO: 1, 3, 5, 7, 9, 11, 13, 15, 17, 19, 21, 23, 25, 27, 29, 31, 33, 35, 37, 39, 41, 43, 45, 47, or combination thereof under high stringency conditions, wherein said conditions comprise 1×SSC, 1% SDS and 0.1-2 mg/ml denatured calf thymus DNA at 65° C.; and an amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48 or combination thereof.

In yet another embodiment, the integrally transformed non-pathogenic, commensal bacterium encodes a *M. tuberculosis* antigen. The TB antigen, for example, is encoded by one of the following nucleic acid sequences: SEQ ID NO: 1, 3, 5, 7, 9, 11, 13, 15, 17, 19, 21, 23, 25, 27, 29, 31, 33, 35, 37, 39, 41, 43, 45, 47, or combination thereof; the coding region of SEQ ID NO: 1, 3, 5, 7, 9, 11, 13, 15, 17, 19, 21, 23, 25, 27, 29, 31, 33, 35, 37, 39, 41, 43, 45, 47, or combination thereof; a complement of SEQ ID NO 1, 3, 5, 7, 9, 11, 13, 15, 17, 19, 21, 23, 25, 27, 29, 31, 33, 35, 37, 39, 41, 43, 45, 47, or combination thereof; a sequence that hybridizes (e.g., under high stringency conditions) to SEQ ID NO: 1, 3, 5, 7, 9, 11, 13, 15, 17, 19, 21, 23, 25, 27, 29, 31, 33, 35, 37, 39, 41, 43, 45, 47, or combination thereof; and a sequence that encodes SEQ ID NO: 2, 4, 6, 8, 10, 12, 14, 16, 18, 20, 22, 24, 26, 28, 30, 32, 34, 36, 38, 40, 42, 44, 46, 48, or combination thereof.

The present invention also relates to integrally transformed bacterium for the delivery of a foreign polypeptide to an individual with a non-pathogenic, commensal bacterium that comprises: a genomic nucleic acid molecule; a nucleic acid molecule having a nucleic acid sequence that encodes the foreign polypeptide, wherein the nucleic acid sequence is inserted into a gene of the genomic nucleic acid molecule whose protein product is expressed in the bacterium's cytoplasm or cell wall or exported to the cell surface of the bacterium; and a nucleic acid molecule having a nucleic acid sequence for the selection of the integrally transformed bacterium. In an aspect, the nucleic acid molecule of the foreign polypeptide expresses an antigen that elicits an immunogenic response in the individual, a vaccine, an inhibitor of a pathogen, an immune booster, a composition used in the treatment of a disease or condition, or a combination thereof. The commensal bacterium can be present or inoculated in an individual in an amount between about $10 \times 10^3$ and about $10 \times 10^{10}$. In an embodiment, the bacterium is commensal to the oral cavity, the upper respiratory tract, or both.

The present invention also relates to systems for delivering, to an individual, one or more foreign polypeptides that are integrally transformed into non-pathogenic bacteria. The system includes a non-pathogenic, commensal bacterium having a genomic nucleic acid molecule; and a nucleic acid molecule having a nucleic acid sequence that encodes the foreign polypeptide, wherein the nucleic acid sequence is inserted into a gene of the genomic nucleic acid molecule that encodes a polypeptide presented on the cell wall of the bacterium. The nucleic acid molecule of the foreign polypeptide can be an antigen that elicits an immunogenic response in the individual, a vaccine, an inhibitor of a pathogen, an immune booster, a modulator, a composition used in the treatment of a disease or condition, or a combination thereof. The bacteria can include, for example, *Streptococcus mitis, Streptococcus oxalis, Streptococcus sanguis, Streptococcus salivarius, Streptococcus constellatus, Lactobacillus casei, Lactobacillus fermenti, Veillonella parvula, Prevotella melaninogenica, Eikenella corrodens, Neisseria mucosa, Actinomyces odontolyticus, Fusobacterium periodonticum, Borrelia vincentii,* and *Actinomyces naeslundii*. The polypeptide expressed by the integrally transformed non-pathogenic, commensal bacterium is described herein.

The present invention relates to methods of delivering a foreign protein to an individual to induce mucosal immunity. The method includes the steps of contacting the integrally transformed non-pathogenic, commensal bacterium, as described herein, with tissue of the oral cavity or upper respiratory tract of the individual in an amount sufficient for colonization of the bacteria. The amount of the integrally transformed bacterium that is contacted with the oral cavity or upper respiratory tract ranges, for example, between about $1 \times 10^3$ and about $1 \times 10^{10}$. The method can further include subjecting the individual to an antibiotic prior to contacting the integrally transformed non-pathogenic, commensal bacterium with the individual. The method can also include inserting a nucleic acid molecule that expresses the foreign polypeptide into a gene into the genome of the bacterium that expresses or secretes a cell-wall surface protein. Also, the methods can further include ligating a construct comprising a vector having the nucleic acid molecule that encodes the foreign polypeptide, into the gene in the genome of the bacterium that expresses or secretes a cell-wall surface protein.

The characteristics of the immune response elicited through a mucosal route of vaccination have a number of advantages over parenteral vaccination. First, mucosal immunization results in an abundant production of antigen-specific IgA antibodies at the site of infection. This pathogen-specific response is important not only for the prevention of infection in vaccinated individual, but also helpful in the prevention of a healthy carrier condition and subsequent pathogen transmission to unprotected individuals. Second, in addition to IgA responses, mucosal vaccination elicits systemic IgG responses that correspond to a further defense against pathogens. Such synergistic stimulation of mucosal and systemic antibody production is important for protection against pathogens such as HIV that can infect through both mucosal and systemic route. Third, mucosal immunization at one site results in specific responses at distant sites due to mucosal lymphocyte migration and expression of homing receptors. This is important because defensive immunity against sexually transmitted diseases, for example, can be acquired through oral immunization. Fourth, besides serum IgG and mucosal IgA antibodies, mucosal vaccines have the ability to engage cell mediated responses including T helper and cytotoxic T cell responses, which are important for intracellular pathogen clearance.

Mucosal administration of vaccines is also associated with certain important practical advantages. It is non-invasive, does not require the use of needles, eliminates the need for expensive specialized personnel, and is characterized by reduced adverse effects. The development of efficacious vaccines to serious infectious diseases such as tuberculosis and AIDS has an incalculable commercial potential. The extremely high incidence, morbidity and mortality of these diseases associated with the lack of existing vaccines to them, constitute by definition a solid foundation for investment and commercialization of the final product.

BRIEF DESCRIPTION OF THE DRAWINGS

FIG. 1 is a bar graph showing relative abundance of different strains of commensal bacteria in human oral cavity samples from 225 healthy subjects as determined by DNA-DNA hybridization assay.

Figure 2:
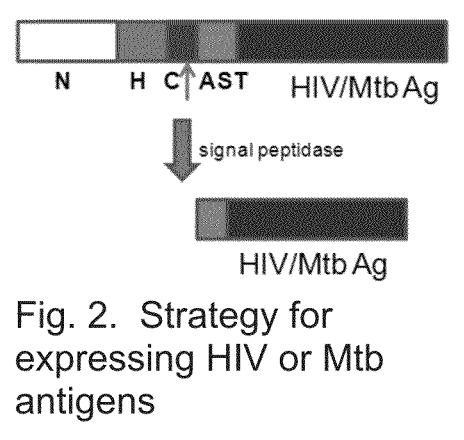

FIG. 2 is a schematic illustrating the strategy for integrating genes for HIV or M. tuberculosis antigens at the 5'end of the S. mitis pullulanase gene encoding a signal peptide that allows processing and secretion of the M. tuberculosis and HIV antigens. The signal peptide consists of several regions including amino terminal end region (N), a hydrophobic core (H) encoding the transmembrane domain of the peptide, a signal peptidase cleavage site (C), and an accessory sequence transport motif (AST).

FIG. 3 is a schematic illustrating the strategy for the transformation of *S. mitis. M. tuberculosis* antigen 85b, HIV antigen HXBc2 or erythromycin resistance gene (ermR) were stably transformed into pulA/SMT0163 gene via homologous recombination. DNA fragments containing either ermR alone (control), HIV/ermR, or 85b/ermR flanked by 250 bp pulA 5' and 3' fragments were ligated into a suicide vector (pCR2.1) for transformation and integration at the pulA locus. The table provides the transformation efficiency of each construct by selection on erythromycin containing plates.

FIG. 4 is a schematic illustrating the results of the genomic polymerase chain reaction (PCR) analysis demonstrating successful integration of HIV HXBc2 gene in the *S. mitis. S. mitis* specific, HIV specific, and ermR specific fragments were amplified using *S. mitis* specific primer set A/B, HIV specific primer C, and ermR-specific primer D. Electrophoresis gel image demonstrates that primers A/B generated the expected 250 bp smt0163 PCR product, while primers C and D generated the expected 1 kb product.

FIG. 5 is a schematic illustrating the results of the genomic PCR analysis demonstrating successful integration of TB 85b gene in the *S. mitis*. Electrophoresis gel image demonstrates that pulA specific primer x and 85b specific primer y generate the expected 250 bp fragment (lanes 2 and 3).

FIG. 6A is a schematic representation of HIV gp120 gene containing C-terminal His-tag incorporated into pulA gene by homologous recombination.

FIG. 6B is a Western blot image demonstrating successful expression of HIV gp120 antigen (approx. 70 kD peptide fragment) detected by anti-His-tag antibody in recombinant *S. mitis* cell lysate (lane 3), but not in parent *S. mitis* cell lysate (lane 2). His-tagged *M. tuberculosis* protein was used as a positive control (lane 1).

FIG. 6C is a Western blot image demonstrating successful expression of secreted HIV gp120 antigen (approx. 70 kD peptide) detected by anti-His-tag antibody in bacterial culture supernatant (lane 2 and 4), but not in the supernatant from the parent *S. mitis* (lane 5-7). His-tagged *M. tuberculosis* protein was used as a positive control (lane 1).

FIG. 7A is a table illustrating the stability of the recombinant *S. mitis* vector over 30 generations of replication without antibiotic. Four clones HIVgp120A-D were grown without antibiotic for 30 generations of replication. The table expresses the stability of the recombinant vector as a number of ermR colonies over the total number of colonies streaked FIG. 7B is a Western blot showing that the expression of HIV gp120 antigen remains unchanged over the 30 generations of replication.

FIGS. 8A and B are graphical representations showing the ability of *rS. mitis* to elicit HIV-specific immune response in mice. Intracellular cytokine staining in CD4+ (FIG. 8A) and CD8+ (FIG. 8B) T cells is illustrated in a series of dot plots. IFNγ, TNFα, and IL-2 positive cells are detected in HIV-1 immunized animals, but not in saline treated control animals.

FIGS. 9A and B are graphical representations showing the ability of *rS. mitis* to elicit HIV-specific immune response in mice. Intracellular cytokine staining in CD4+ (FIG. 9A) and CD8+ (FIG. 9B) T cells is illustrated in a series of dot plots. IFNγ, TNFα, and IL-2 positive cells are detected in HIV-1 immunized animals, but not in sham treated control animals.

FIGS. 10A-10G are schematics showing the nucleic acid sequences (in Bold) (SEQ ID NO: 1, 3, 5, 7, 9, 11, 13, 15, 17, 19, 21, 23, 25, and 27) and corresponding *M. tuberculosis* polypeptide sequences (in Bold) (SEQ ID NO: 2, 4, 6, 8, 10, 12, 14, 16, 18, 20, 22, 24, 26, and 28) eluted from MHC class 1 molecules from the macrophages of mice infected with the *M. tuberculosis* bacteria.

FIG. 10H is a table showing *M. tuberculosis* peptide sequences, SEQ ID Nos: 2, 6, 10, 14, 18, 22, and 26, eluted from MHC class 1 molecules from the macrophages of mice infected with the *M. tuberculosis* bacteria. The figure also shows The Institute for Genomic Research (TIGR) annotation, the Swiss-Prot designation, and the protein name.

FIG. 11 is a schematic showing a peptide, SEQ ID NO: 30, in bold, found in the urine of patients with pulmonary tuberculosis, and its corresponding nucleic acid sequence, SEQ ID NO: 29. The figure also shows a DNA sequence (SEQ ID NO: 31) and its corresponding protein sequence (SEQ ID NO: 32) which is a putative molybdopterin biosynthesis protein that is found in *M. tuberculosis* and has 100% homology to SEQ ID NO: 30.

FIG. 12 is a table showing *M. tuberculosis* peptide sequences, SEQ ID Nos: 34, 38, 42, and 46, found in the urine of patients with pulmonary tuberculosis and the *M. tuberculosis* donor protein.

FIGS. 13A-B are schematics showing the nucleic acid sequence (in Bold and Underline) (SEQ ID NO: 33) and corresponding *M. tuberculosis* polypeptide sequence (in Bold and Underline) (SEQ ID NO: 34) found in the urine of patients with pulmonary tuberculosis. Also depicted are homoserine O-acetyltransferase nucleic acid and polypeptide sequences from *M. tuberculosis* having 100% homology to the isolated sequences (SEQ ID NOs: 35 and 36, respectively), along with a table providing TIGR locus name, primary locus name, the Swiss-Prot designation, putative identification, gene symbol, TIGR cellular roles, coordinates, DNA molecule name, gene length, protein length, molecular weight, pl, percent GC, enzyme Commission #, Kingdom, and Family.

FIGS. 14A-C are schematics showing the nucleic acid sequence (in Bold and Underline) (SEQ ID NO: 37) and corresponding *M. tuberculosis* polypeptide sequence (in Bold and Underline) (SEQ ID NO: 38) found in the urine of patients with pulmonary tuberculosis. Also depicted are Chromosome partition protein smc nucleic acid and polypeptide sequences from *M. tuberculosis* having 100% homology to the isolated sequences (SEQ ID NOs: 39 and 40, respectively), along with a table providing the TIGR locus name, primary locus name, the Swiss-Prot designation, putative identification, gene symbol, TIGR cellular roles, coordinates, DNA molecule name, gene length, protein length, molecular weight, pI, percent GC, enzyme Commission #, Kingdom, and Family.

FIGS. 15 A-B are schematics showing the nucleic acid sequence (in Bold and Underline) (SEQ ID NO: 41) and corresponding *M. tuberculosis* polypeptide sequence (in Bold and Underline) (SEQ ID NO: 42) found in the urine of patients with pulmonary tuberculosis. Also depicted are ornithine carbamoyltransferase nucleic acid and polypeptide sequences from *M. tuberculosis* having 100% homology to the isolated sequences (SEQ ID NOs: 43 and 44, respectively), along with a table providing the TIGR locus name, primary locus name, the Swiss-Prot designation, putative identification, gene symbol, TIGR cellular roles, coordinates, DNA molecule name, gene length, protein length, molecular weight, pI, percent GC, enzyme Commission #, Kingdom, and Family.

FIGS. 16A-B are schematics showing the nucleic acid sequence (in Bold and Underline) (SEQ ID NO: 45) and corresponding *M. tuberculosis* polypeptide sequence (in Bold and Underline) (SEQ ID NO: 46) found in the urine of patients with pulmonary tuberculosis. Also depicted are phosphoadenosine phosphosulfate reductase nucleic acid and polypeptide sequences from *M. tuberculosis* having 100% homology to the isolated sequences (SEQ ID NOs: 47 and 48, respectively), along with a table providing the TIGR locus name, primary locus name, the Swiss-Prot designation, putative identification, gene symbol, TIGR cellular roles, coordinates, DNA molecule name, gene length, protein length, molecular weight, pI, percent GC, enzyme Commission #, Kingdom, and Family.

FIGS. 17A and B are sequence listings showing the nucleic acid sequence (SEQ ID NO: 53) and corresponding polypeptide sequence (SEQ ID NO: 54) of the pula signal peptide.

FIGS. 17C and D are sequence listings showing the nucleic acid sequence (SEQ ID NO: 51) and corresponding polypeptide sequence (SEQ ID NO: 52) of the pulaHIVgp120 fusion protein.

FIG. 17E is a sequence listing showing the nucleic acid sequence (SEQ ID NO: 49) and corresponding polypeptide sequence (SEQ ID NO: 50) of the HIV T20 antigen.

DETAILED DESCRIPTION OF THE INVENTION

A description of preferred embodiments of the invention follows.

The present invention relates to compositions and methods for inducing mucosal immunity using an integrally transformed non-pathogenic commensal bacterium in the oral cavity, upper respiratory tract or both. A foreign polypeptide is integrally transformed into a commensal bacterium to be used as a mucosal vaccine.

Mucosal immunity is important for certain diseases such as tuberculosis and acquired immunodeficiency disease syndrome (AIDS). The main protective mechanism of the injectable vaccines is the induction of serum antibodies, mainly IgG, which prevent systemic spread of the pathogen and which can also, through transudation, exert a minor local protective effect at the mucosal surfaces. Mucosal vaccination, however, induces an immune response that more closely resembles natural immunity than the response elicited by injectable vaccine. Mucosally administered vaccine will induce a much stronger mucosal immunity characterized by significantly higher local IgA antibodies and local cell mediated immunity than the injectable vaccine.

Prior to the present invention, formulations and vaccine delivery systems that targeted the development of a strong mucosal immunity were not tested. Nonetheless, the lung and other mucosal structures are an important battleground site for the successful establishment of infections like tuberculosis, AIDS and other infections. Additionally, the compositions of the present invention utilize immunization protocols that generate and maintain a continuous supply of both effector and long-lived memory T cells. This is an important issue because resistance mediated by effector T cells should be highly dependent on the continuous activation of these cells, which are capable of recognizing invading organisms and quickly respond with production of mediators of resistance like IFN-γ.

Commensal Bacteria:

An important innovative aspect of the present invention is the utilization of the commensal oral organism, *S. mitis*, as opposed to attenuated strains of virulent bacteria (and viruses) that were previously tested as live antigen delivery vectors. Examples of these systems are *Salmonella* enteric serovar *typhi* (*S. typhi*) and enteric serovar *typhimurium* (*S. typhimurium*), *Shigella, Vibrio cholerae, Listeria monocytogenes, Mycobacterium bovis* (Bacille Calmette-Guerin, BCG), and *Yersinia enterocolitica*. These vectors impose several restrictions on the downstream steps of vaccine development for human use including poor safety performance and poor long-term colonization. In contrast, *S. mitis* is an excellent commensal colonizer and abundantly present in the mucosal areas of the normal human oral cavity (FIG. 1) and there are no pending safety issues with the organism making it a highly attractive for use as a delivery vector for mucosal immunization.

Commensal bacteria are those that are found in the natural flora of living organisms. Commensal bacteria reside mainly within mucosal sites such as mouth, nose, lungs, gastrointestinal and urogenital tracts. Commensal bacteria are also defined as non-pathogenic, meaning that these organisms do not cause disease or conditions that are harmful to the host. Not only do they not cause harm, but also commensal populations are believed to keep pathogenic species in check by not allowing them to adhere to mucosal surfaces. Besides presenting physical barriers to invading pathogens, mucosal surfaces possess specific local immune systems that provide an important component of protective immunity. Antigen delivery directly to mucosal sites via non-pathogenic commensal bacterial vectors provide a substantial advantage over some of the more conventional vaccines in that live bacteria are capable of stimulating persistent systemic as well as local immune responses. Additionally, commensal bacteria are able to colonize the niche invaded by the pathogen and stimulate an immune response at their portal of entry to prevent infection. Commensal bacteria are used with the compositions and methods of the present invention as a delivery vehicle because they colonize well, and are easily administered, cost efficient, and well-tolerated.

*S. mitis* is a Gram-positive commensal bacterium (class: bacilli) that abundantly colonizes mucosal surfaces of the oral cavity and upper respiratory tract. *S. mitis* is generally not motile, does not form spores and lacks group-specific antigens. *S. mitis*, as well as other strains of commensal bacteria, possesses excellent adjuvant activity for stimulation of cell-mediated immune response, induction of long-term immunological memory and is a very safe candidate for use in recombinant vaccines. Many strains of commensal bacteria that reside on mucosal surfaces are excellent candidates for use as vaccine vehicles into which genetic material of interest can be introduced and successively expressed. The present invention describes such bacterial vehicles for vaccine delivery, whereas integrally transformed non-pathogenic, commensal bacteria is used to express a peptide antigen. Examples of such bacteria include *Streptococcus mitis, Streptococcus oxalis, Streptococcus sanguis, Streptococcus salivarius, Streptococcus constellatus, Lactobacillus casei, Lactobacillus fermenti, Veillonella parvula, Prevotella melaninogenica, Eikenella corrodens, Neisseria mucosa, Actinomyces odontolyticus, Fusobacterium periodonticum, Borrelia vincentii,* and *Actinomyces naeslundii.*

Figures 7A, 7B:
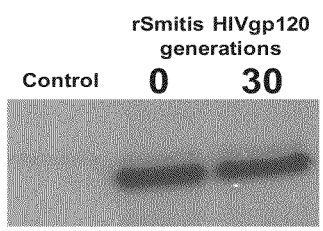

Foreign Polypeptides:

Recombinant commensal bacteria of the present invention are engineered to express foreign polypeptides either on their cell-wall surface or in the secreted form. As used herein, the term "foreign polypeptide" encompasses amino acid chain of any length, including full length proteins (i.e., antigens), wherein their sequence is not encoded by the endogenous bacterial DNA. Foreign polypeptide, in this case, can be any foreign antigen that elicits an immunogenic response including but not limited to a vaccine antigen, an immune booster or modulator of the immune response, pathogen inhibitor, or any combination of the above.

Vaccine antigen used with the compositions of present invention refers to any foreign polypeptide that elicits a protective cell mediated and/or humoral immune response and results in a long-term immunological memory. There are several types of antigen-based vaccines including purified and recombinant vaccines. Purified antigen vaccines, also referred to as subunit vaccines, are composed of molecules purified directly from the pathogenic organisms. Purified antigen vaccines identify molecules that generate a protective immune response including structural proteins, polysaccharides, and chemically inactivated or attenuated bacterial toxins (exotoxins). Examples of purified antigen vaccines include *Streptococcus pneumoniae* and *Neisseria meningitidis* polysaccharides, and *Clostridium tetani* toxin. Most purified antigen vaccines require the use of adjuvant to elicit a strong immune response and multiple immunizations are often required.

Recombinant antigen vaccines are composed of immunogenic proteins produced by genetic engineering. DNA encoding for an immunogenic protein of a pathogen can be inserted into either bacteria, yeast, viruses which infect mammalian cells, or by transfection of mammalian cells. The cells will then produce the protein endogenously and the protein can be harvested.

Recombinant vector vaccines utilize the attenuated versions of certain microbes as recombinant vectors to express target antigens from other pathogens. The major advantage of recombinant vector vaccines is the ability to generate both humoral and cell-mediated immune responses resulting in stronger, longer-lasting protection. The present invention encompasses methods for the development of recombinant vector vaccines based on commensal bacteria stably transformed with constructs encoding the following: *M. leprae* antigens, *M. tuberculosis* antigens, *M. africanum* antigens, *M. intracellulare* antigens, *M. avium* antigens, *Treponema* antigens, Pertussis antigens, Herpes virus antigens, Measles virus antigens, Mumps virus antigens, *Shigella* antigens, *Neisseria* antigens, *Borrelia* antigens, Rabies virus antigens, polio virus antigens, human immunodeficiency virus antigens, snake venom antigens, insect venom antigens, hepatitis A, B, C virus, human papilloma virus antigens, *Vibrio cholera*, and fungus organisms such as *Candida albicans, Candida tropicalis, Paracoccidioides brasiliensis* etc. Specific examples include TB and HIV antigenic peptide sequences listed below (SEQ ID NO: 2, 4, 6, 8, 10, 12, 14, 16, 18, 20, 22, 24, 26, 28, 30, 32, 34, 36, 38, 40, 42, 44, 46, 48, or combinations thereof, shown in FIGS. 10-16) and HIV sequences (SEQ ID NO:50, 52 shown in FIG. 17).

An Inhibitor of a Pathogen:

The present invention also describes the development of therapeutic vaccines based on recombinant commensal bacteria expressing a pathogen inhibiting peptide. An inhibitor of pathogen can include any peptide that prevents or reduces the host infection by pathogen by either of the following means inhibition of pathogen interaction with host receptor necessary for infection, inhibition of pathogen replication at the site of entry into the host, inhibition of the assembly of newly formed pathogenic entities (relevant for viral pathogens), and neutralization of toxins released by pathogenic organisms (relevant for bacterial pathogens). One example described in the present invention includes a potent HIV inhibitor peptide, T20, which is a 36 amino acid peptide, expressed by a recombinant *S. mitis*, that acts as a decoy α-helix and prevents HIV-1 infection by disrupting the assembly of the six-helix bundle viral fusion apparatus by mimicking the heptad repeat 2 (HR2) oligomerization domain of the gp41 envelope glycoprotein. Additionally, present invention includes a foreign polypeptide that includes HIV antigen as follows: gp120 env, gp140 env, gp160 env, gag, pol, nef, vif, vpr, vpu, tat, rev, nef or HIV T20. Additional sequences can be designed to express inhibitors of the following pathogens: *Mycobacterium tuberculosis; Mycobacterium leprae; Mycobacterium africanum; Mycobacterium intracellulare; Mycobacterium avium*; Malaria; Diphtheria; *Leishmania; Salmonella; Treponema*; Pertussis; Herpes virus; Measles virus; Mumps virus; *Shigella; Neisseria; Borrelia*; rabies virus; polio virus; Human immunodeficiency virus type I and II; Hepatitis A, B, C virus, *Vibrio cholera*; and fungus organisms such as *Candida albicans, Candida tropicalis, Paracoccidioides brasiliensis* etc. TB vaccines and *Mycobacterium* vaccine antigens are described in U.S. Pat. No. 7,968,694.

An Immune Booster and a Modulator:

The present invention describes the use of additional sequences encoding immune booster and modulator for generation of recombinant commensal bacteria based vaccine. Several classes of immune boosters and modulators can be defined, including: interferons, interleukins, and other cytokines. Certain mucosal vaccine antigens do not have the ability to induce a potent adaptive immune response and significant immunoglobulin production and therefore an appropriate adjuvant may be required. Cytokines are powerful modulators of the immune response that have the ability to trigger both adaptive and innate immune response by stimulating Th1 and Th2 responses, maturation of antigen presenting cells, and induction of NK cells and CTLs. Therefore, cytokines can be used as potent mucosal vaccine adjuvants for enhancing the immune response against infectious pathogens. Interferons play an important role in the defense against viral pathogens. They are part of innate immune response and often induced at an early stage during viral infection. Interferons typically stimulate the cells of the innate immune system to increase the expression of MHC molecules and promote more efficient antigen presentation to helper T cells. Therefore, interferons can also be useful adjuvants in the development of recombinant mucosal vaccines. Examples of immune boosters and modulators include: Interleukins, interferons, and cytokines such as IL-1, IL-2, IL-4, IL-6, IL-8, IL-12, IL-17, IL-2 IL-21 and IL-22 and cytokines GMCSF, MCSF, MIP1alpha and beta, TNFalpha and beta, IFNalpha and beta and TGFbeta.

Integrative Transformation:

Bacterial transformation is defined as introduction of foreign genetic material in the form of a DNA plasmid or fragment into bacterial cells resulting in incorporation and expression of exogenous genes by the transformed bacteria. Bacteria that can be transformed are referred to as "competent." Different methods exist for the induction of bacterial competence including calcium chloride based transformation and electroporation. The mechanism of competence induction is based on the ability to create pores in the cell membrane of the bacteria, which allows passive uptake of plasmid DNA into bacterial cells. Plasmids are small circular pieces of DNA of about 2,000 to 10,000 base pairs that may or may not contain important genetic information for the growth of bacteria. The main components of a plasmid include the origin of replication, multiple cloning site, and antibiotic resistance gene. Recombinant plasmid vectors can be created by introducing a gene of interest into a multiple cloning site followed by selection on antibiotic containing growth media. Transformed bacterial cells containing newly introduced plasmid become antibiotic resistant and successfully survive on antibiotic-rich media. A self-replicating recombinant vector, in this case, is propagated in the bacteria independently of the bacterial genome.

In contrast, integrative transformation describes the stable introduction of the whole or part of a recombinant vector into the bacterial genome itself. A construct of interest can be engineered to replace one allele in the genome without affecting any other locus of the bacterial chromosome. The method of choice for a stable introduction of a construct into the bacterial genome is known as "homologous recombination." DNA sequence of the gene to be replaced is known in order to engineer a construct for homologous recombination. The sequence of an engineered construct includes some flanking DNA on both sides that is identical in sequence to the targeted locus.

The present invention encompasses the construction of a vector for stable integration of the genes coding, for example for *M. tuberculosis* Ag85b and HIV1 HXBc2 env-His-tag antigens into the genome of *S. mitis*. These genes were integrated into the signal sequence of pulA gene, coding for the pullulanase enzyme. Pullulanase is an amylolytic exoenzyme that is produced as a cell-surface anchored lipoprotein by Gram-positive bacteria. PulA was selected as an integration site because the gene has a strong promoter and encodes localization motifs for the gene product; furthermore, pulA is not essential for bacterial growth. The recombinant vector was generated by incorporating sequences encoding *M. tuberculosis* and HIV antigens preceded by an accessory sequence transport motif (AST) next to the peptidase cleavage site (C) (FIG. 2). For stable expression, the *M. tuberculosis* and HIV antigen encoding genes along with ermR cassette, flanked on both sides by 250 bp pulA 5' and 3' fragments, were integrated via homologous recombination into the pulA gene of *S. mitis* (FIGS. 3-5). Another vector was constructed in the same manner to incorporate HIV Env gene into *S. mitis* by homologous recombination (FIG. 6).

Methods for Immunizing:

Once a foreign gene has been integrated into the genome of the commensal bacterium, the integrant bacteria, such as those of the present invention, can be introduced to an individual in need thereof. The methods of the present invention include methods for vaccinating an individual by inoculating the individual with the integrant commensal bacteria having the foreign polypeptide. Inoculating procedures can include swabbing, spraying, inhaling or otherwise introducing the integrated commensal bacteria to the oral cavity or upper respiratory system. The integrated commensal bacteria used in the invention can be administered nasally, topically, or by inhalation.

The commensal bacteria should be administered/inoculated in amounts sufficient to result in colonization of the bacteria in the oral cavity, upper respiratory tract, or both. The composition can be administered in a single dose or in more than one dose over a period of time so that the bacteria colonize and the foreign polypeptide confers the desired effect (e.g., is administered to the individual and the individual obtains immunity).

The actual effective amounts of integrant commensal bacteria of the present invention, delivered with or without a carrier, can vary according to the specific composition being utilized, the mode of administration and the age, weight and condition of the patient. For example, as used herein, an effective amount of bacteria is an amount which allows the bacteria to colonize in the oral cavity and/or upper respiratory system. Dosages for a particular individual patient can be determined by one of ordinary skill in the art using conventional considerations (e.g. by means of an appropriate, conventional pharmacological protocol). In an embodiment, the amount of the commensal bacteria of the present invention used to inoculate an individual ranges in an amount between about $10 \times 10^3$ and about $10 \times 10^{10}$.

For enteral or mucosal application (including via oral and nasal mucosa), particularly suitable are liquids, drops, or suppositories. A syrup, elixir or the like can be used wherein a sweetened vehicle is employed. Liposomes, microspheres, and microcapsules are available and can be used.

Pulmonary administration can be accomplished, for example, using any of various delivery devices known in the art such as an inhaler. See. e.g., S. P. Newman (1984) in *Aerosols and the Lung*, Clarke and Davis (eds.), Butterworths, London, England, pp. 197-224; PCT Publication No. WO 92/16192; PCT Publication No. WO 91/08760.

The administration of the commensal bacteria (integrants) of the present invention can occur simultaneously or sequentially in time in conjunction with other conventional vaccination systems and protocols or in isolation. A commensal bacterium and/or pharmaceutical composition as described above can be administered simultaneously with or sequentially with an immune enhancer, or other compound known in the art that would be administered with such a vaccine. The compound can be administered before, after or at the same time as the integrated commensal bacteria of the present invention. Thus, the term "co-administration" is used herein to mean that the integrated commensal bacteria and the additional compound (e.g., immune stimulating compound) will be administered at times to achieve an immune response, as described herein. The methods of the present invention are not limited to the sequence in which the compounds are administered, so long as the compound is administered close enough in time to produce the desired effect.

Routes and frequency of administration of the inventive pharmaceutical compositions and vaccines, as well as dosage, will vary from individual to individual or from system to system. In general, the pharmaceutical compositions and vaccines can be administered intranasally or orally. An example of the protocol for inoculating an individual with integrated commensal bacteria is as follows: inoculate three times, one month apart between inoculations.

The compositions of the present invention are preferably formulated as either pharmaceutical compositions or as vaccines for in the induction of protective immunity against the foreign polypeptide in a patient. A patient can be afflicted with a disease, or can be free of detectable disease and/or infection. In other words, protective immunity can be induced to prevent, reduce the severity of, or treat the disease associated with the foreign bacteria.

In one embodiment, pharmaceutical compositions of the present invention comprise one or more of the integrated commensal bacteria, and a physiologically acceptable carrier. Similarly, integrated commensal bacteria comprise one or more the above polypeptides and a non-specific immune response enhancer, such as an adjuvant or a liposome (into which the polypeptide is incorporated).

The integrant commensal bacteria of the present invention can be administered with or without a carrier. The terms "pharmaceutically acceptable carrier" or a "carrier" refer to any generally acceptable excipient or drug delivery composition that is relatively inert and non-toxic. Exemplary carriers include sterile water, salt solutions (such as Ringer's solution), alcohols, gelatin, talc, viscous paraffin, fatty acid esters, hydroxymethylcellulose, polyvinyl pyrolidone, calcium carbonate, carbohydrates (such as lactose, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.). Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include, potassium sorbate, sodium metabisulfite, methyl paraben, propyl paraben, thimerosal, etc. The compositions can also be combined where desired with other active substances, e.g., enzyme inhibitors, to reduce metabolic degradation. A carrier (e.g., a pharmaceutically acceptable carrier) is preferred, but not necessary to administer the compound.

The composition can be a liquid solution, suspension, emulsion, sustained release formulation, gel, mist, or spray. The method of administration can dictate how the composition will be formulated. For example, the composition can be formulated as a suppository, with traditional binders and carriers such as triglycerides.

Measuring the Immunogenicity of the Vaccine:

Once the commensal bacteria are administered to the individual, an individual can be assessed to determine if the vaccine provided an immunogenic response to the foreign polypeptide. The efficacy of a mucosal immunization can be measured by determining the immunogenic response of the person who received the vaccine. The foreign peptides described herein expressed on the surface of recombinant *S. mitis* (rS. mitis) have the ability to elicit an immune response. More precisely, administration of rS. mitis results in activation of the components of cell mediated immunity, specifically CD4+ and CD8+ T cells, NK cells, B cells and/or macrophages, leading to proliferation and cytokine production including but not limited to IFNγ, TNFα and IL-2 in an immunized individual. Immunological evaluation methods for cell mediated immune response include antigen specific stimulation of cells followed by measurements of secreted cytokines by enzyme-linked immunosorbent assay (ELISA) or multiplex bead assay, measurement of intracellular cytokine levels by flow cytometry, as well as measurements of cell proliferation.

The ability of a polypeptide or bacterial lysate to stimulate the secretion of cytokines can be evaluated by contacting the cells with the polypeptide and measuring cytokine levels in the supernatant. In general, the amount of polypeptide that is sufficient for the evaluation of about $10^5$ cells ranges from about 10 ng/mL to about 100 μg/mL and preferably is about 10 μg/mL. The polypeptide can, but need not, be immobilized on a solid support, such as a bead or a biodegradable microsphere, such as those described in U.S. Pat. Nos. 4,897,268 and 5,075,109. The incubation of polypeptide with the cells is typically performed at 37° C. for about six days. Following incubation with polypeptide, the culture supernatants are assayed for IFN-γ (and/or TNFα and IL-2), which can be evaluated by methods known to those of ordinary skill in the art, such as an enzyme-linked immunosorbent assay (ELISA). In general, a polypeptide that results in the production of at least 50 pg of interferon γ per mL of cultured supernatant (containing $10^4$-$10^5$ T cells per mL) is considered able to stimulate the production of IFN-γ. A polypeptide that stimulates the production of at least 100 pg/mL of TNF α, and/or at least 10 U/mL of IL-2, per $10^5$ T cells (or per $3 \times 10^5$ PBMC) is considered able to stimulate the production of TNF α and/or IL-2.

Figure 8B:
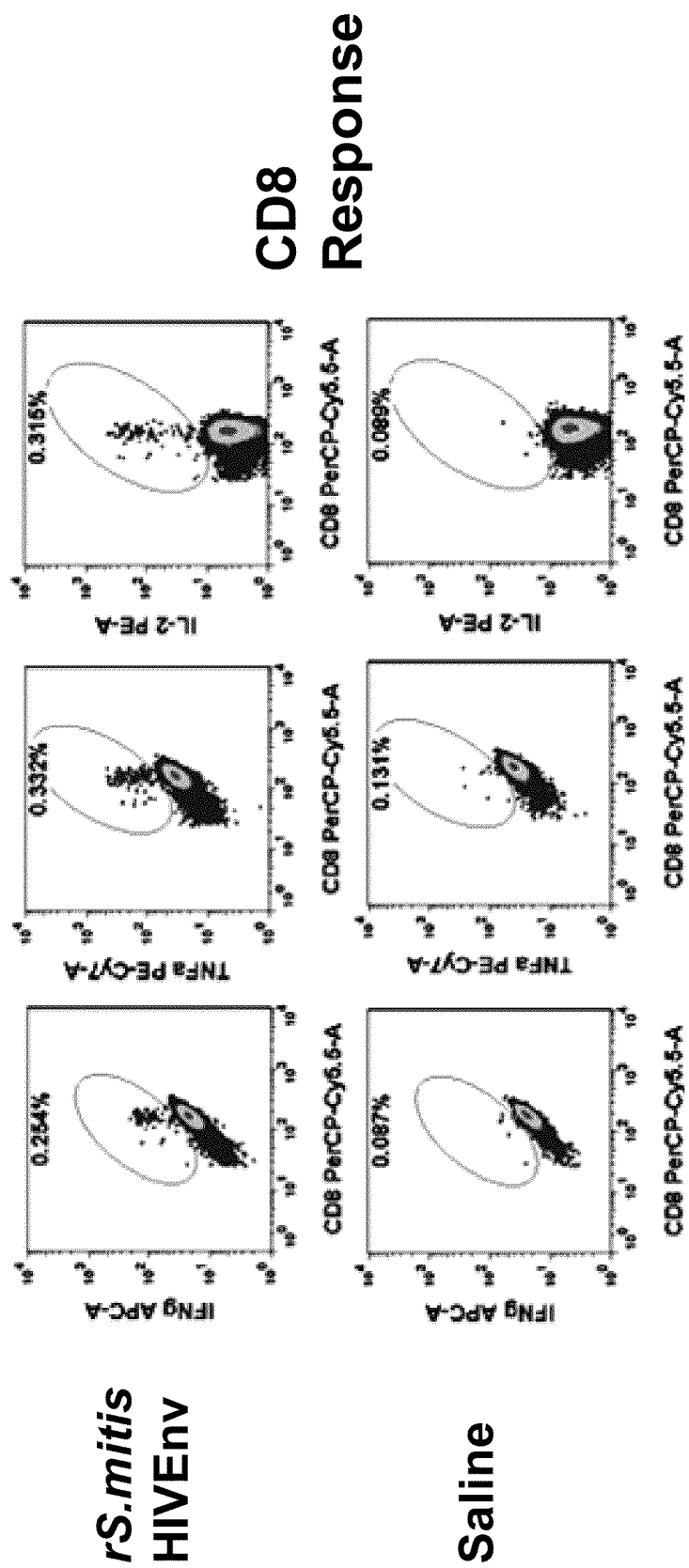
Figure 9A:
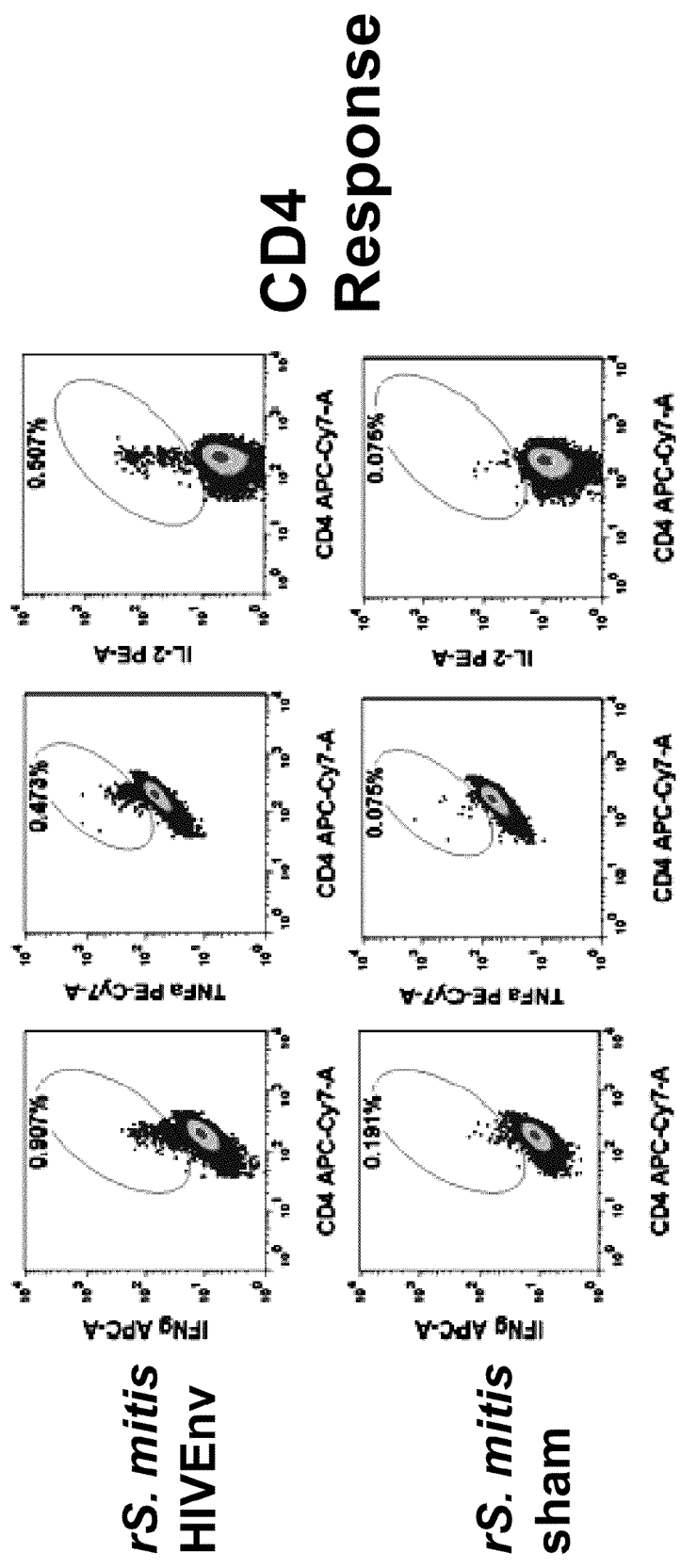
Figure 9B:
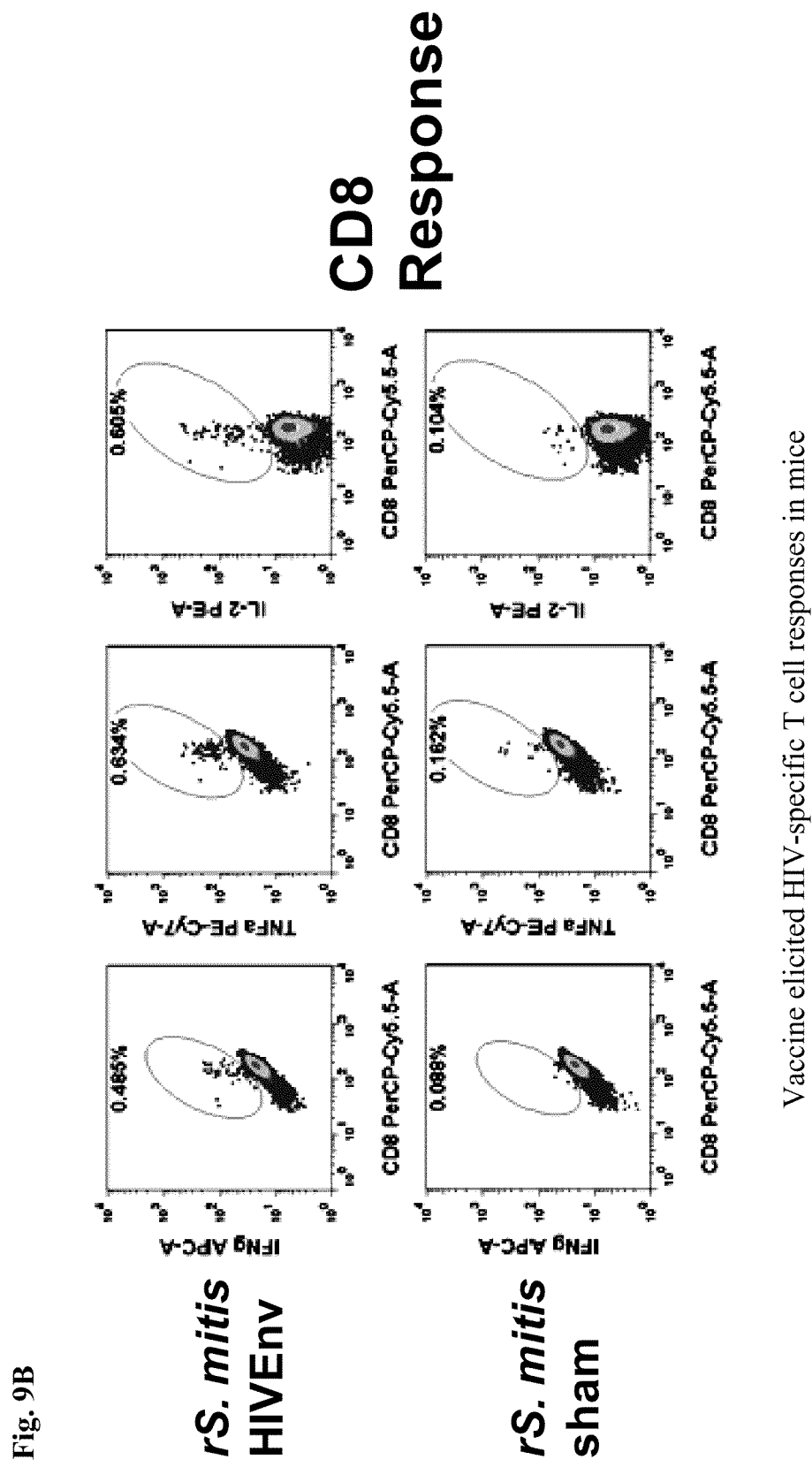

Intracellular cytokine staining is a flow cytometric technique that can detect single cell expression of cytokines and allows simultaneous detection, quantitation, and phenotypic characterization of antigen-specific T cells in PBMC. In this multiparametric flow cytometry based method, antigen specific T cells are identified based on their intracellular accumulation of a cytokine in conjunction with their characteristic CD4+ and CD8+ T cells, activation, effector, memory and mucosal homing surface markers following antigenic stimulation of PBMC. Intracellular cytokine staining assay is performed on PBMC isolated from whole blood of immunized individual by Ficoll gradient centrifugation. Cells are then restimulated by contact with polypeptide (e.g., an immunogenic antigen, or a portion or other variant thereof) or recombinant bacterial lysate for 6-10 hours at 37 C. Restimulated cells are then permeabilized and contacted with fluorescently labeled monoclonal antibodies against interferon γ, TNFα, IL-2, and granzyme) as well as antibodies against surface markers characteristic for particular cell type. Percent of IFN-γ, TNFα, and IL-2 positive cells is then determined using appropriate software (FIGS. 8, 9). A polypeptide that stimulates statistically significant increase in the number of IFN-γ, TNFα, and IL-2 positive cells when compared to control is considered able to stimulate cytokine production.

Polypeptides and their Function:

The present invention relates to polypeptide molecules encoded by the recombinant commensal bacteria including antigenic portions of TB, HIV, *Plasmodium, Leishmania*, herpes virus, or hepatitis virus. The present invention includes polypeptide molecules that are encoded by the nucleic acid of the recombinant commensal bacteria and which contain the sequence of any one of the antigenic TB amino acid sequences (e.g., SEQ ID NO: 2, 4, 6, 8, 10, 12, 14, 16, 18, 20, 22, 24, 26, 28, 30, 32, 34, 36, 38, 40, 42, 44, 46, 48, or combinations thereof, shown FIGS. 10-16) or HIV sequences (e.g., SEQ ID NO: 50, 52 shown in FIG. 17), or any of the above fused to the pulA signal peptide. The present invention also pertains to polypeptide molecules that are encoded by nucleic acid sequence of the transformed commensal bacteria and that include the nucleic acid sequences of SEQ ID NO: 1, 3, 5, 7, 9, 11, 13, 15, 17, 19, 21, 23, 25, 27, 29, 31, 33, 35, 37, 39, 41, 43, 45, 47, or combinations thereof.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of any of the above named antigens can consist entirely of the immunogenic portion, or can contain additional sequences. The additional sequences can be derived from the native antigens or can be heterologous, and such sequences can (but need not) be immunogenic.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. A variant of a specific antigen will therefore stimulate cell proliferation and/or interferon production in Th1 cells raised against that specific antigen. Polypeptide variants preferably exhibit at least about 70%, more preferably at least about 90% and most preferably at least about 95% homology to the identified polypeptides. For polypeptides with immunoreactive properties, variants can, alternatively, be identified by modifying the amino acid sequence of one of the above polypeptides, and evaluating the immunoreactivity of the modified polypeptide. Such modified sequences can be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged.

Variants can also, or alternatively, contain other modifications, including the deletion or addition of amino acids that have minimal influence on the antigenic properties, secondary structure and hydropathic nature of the polypeptide. For example, a polypeptide can be conjugated to a signal (or leader) sequence at the N-terminal end of the protein which co-translationally or post-translationally directs transfer of the protein. The polypeptide can also be conjugated to a linker or other sequence for ease of synthesis, purification or identification of the polypeptide (e.g., poly-His), or to enhance binding of the polypeptide to a solid support. For example, a polypeptide can be conjugated to an immunoglobulin Fc region.

The present invention also encompasses proteins and polypeptides, variants thereof, or those having amino acid sequences analogous to the amino acid sequences of antigenic polypeptides described herein. Such polypeptides are defined herein as antigenic analogs (e.g., homologues), or mutants or derivatives. "Analogous" or "homologous" amino acid sequences refer to amino acid sequences with sufficient identity of any one of the amino acid sequences so as to possess the biological activity (e.g., the ability to elicit a protective immune response to antigen expressed by commensal bacteria) of any one of the native polypeptides. For example, an analog polypeptide can be produced with "silent" changes in the amino acid sequence wherein one, or more, amino acid residues differ from the amino acid residues of any one of the protein, yet still possesses the function or biological activity of the antigen peptide. Examples of such differences include additions, deletions or substitutions of residues of the amino acid sequence of antigen peptides. Also encompassed by the present invention are analogous polypeptides that exhibit greater, or lesser, biological activity of any one of the proteins of the present invention. Such polypeptides can be expressed by mutating (e.g., substituting, deleting or adding) nucleic acid residues of any of the sequences described herein. Such mutations can be performed using methods described herein and those known in the art. In particular, the present invention relates to homologous polypeptide molecules having at least about 70% (e.g., 75%, 80%, 85%, 90% or 95%) identity or similarity with SEQ ID NO: 2, 4, 6, 8, 10, 12, 14, 16, 18, 20, 22, 24, 26, 28, 30, 32, 34, 36, 38, 40, 42, 44, 46, 48, or combination thereof. Percent "identity" refers to the amount of identical nucleotides or amino acids between two nucleotides or amino acid sequences, respectfully. As used herein, "percent similarity" refers to the amount of similar or conservative amino acids between two amino acid sequences.

Homologous polypeptides can be determined using methods known to those of skill in the art. Initial homology searches can be performed at NCBI against the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., Gene, 73:237-244 (1988) e.g., using default parameters).

Additionally, the individual isolated polypeptides of the present invention are biologically active or functional and play various roles in bacteria as well. For example, an isolated polypeptide, such as SEQ ID NO: 6 is a glutamine-transport transmembrane protein ABC transporter. Likewise, SEQ ID NO: 22 is a cationic amino acid transport integral member protein, and SEQ ID NO: 26 is a cationic transporting P-type ATPase. SEQ ID NO: 32, is a molybdopterin biosynthesis protein. The present invention includes fragments of these isolated amino acid sequences that still possess the function or biological activity of the sequence. For example, polypeptide fragments comprising deletion mutants of the antigenic TB proteins can be designed and expressed by well-known laboratory methods. Fragments, homologues, or analogous polypeptides can be evaluated for biological activity, as described herein.

The present invention also encompasses biologically active derivatives or analogs of the above described antigenic polypeptides, referred to herein as peptide mimetics. Mimetics can be designed and produced by techniques known to those of skill in the art. (see e.g., U.S. Pat. Nos. 4,612,132; 5,643,873 and 5,654,276). These mimetics can be based, for example, on a specific amino acid sequence and maintain the relative position in space of the corresponding amino acid sequence. These peptide mimetics possess biological activity similar to the biological activity of the corresponding peptide compound, but possess a "biological advantage" over the corresponding antigenic TB amino acid sequence with respect to one, or more, of the following properties: solubility, stability and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276. Other forms of the antigenic polypeptides, encompassed by the present invention, include those which are "functionally equivalent." This term, as used herein, refers to any nucleic acid sequence and its encoded amino acid, which mimics the biological activity of the polypeptides and/or functional domains thereof.

Nucleic Acid Sequences, Plasmids, Vectors and Host Cells:

The present invention, in one embodiment, includes an isolated nucleic acid molecule integrated into the commensal bacteria, having a sequence of SEQ ID NO: 1, 3, 5, 7, 9, 11, 13, 15, 17, 19, 21, 23, 25, 27, 29, 31, 33, 35, 37, 39, 41, 43, 45, 47, or combinations thereof. See FIGS. 10-17. The present invention includes sequences as recited in FIGS. 10-17, as well as the coding regions thereof.

As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, substitutions or additions. Such modifications can be readily introduced using standard mutagenesis techniques Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses genomic commensal DNA having isolated nucleic acid sequences that encode TB and HIV polypeptides, and in particular, those which encode a polypeptide molecule having an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, or combinations thereof. These nucleic acid sequences encode polypeptides that stimulate a protective immunogenic response and/or are involved the functions further described herein.

As used herein, an "isolated" gene or nucleotide sequence which is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. In vivo and in vitro RNA transcripts of the present invention are also encompassed by "isolated" nucleotide sequences. Such isolated nucleotide sequences are useful for the manufacture of the encoded antigenic TB polypeptide, for detecting the presence (e.g., by PCR amplification and DNA sequencing) or expression (e.g., by reverse transcription (RT)-PCR and DNA sequencing) of related genes in cells or tissue, and for gene mapping (e.g., by in situ hybridization).

The antigenic nucleic acid sequences of the present invention include homologous nucleic acid sequences. "Analogous" or "homologous" nucleic acid sequences refer to nucleic acid sequences with sufficient identity of any one of the TB nucleic acid sequences, such that once encoded into polypeptides, they possess the biological activity of any one of the antigenic polypeptides described herein. For example, an analogous nucleic acid molecule can be produced with "silent" changes in the sequence wherein one, or more, nucleotides differs from the nucleotides of any one of the polypeptides described herein, yet, once encoded into a polypeptide, still possesses its function or biological activity. Examples of such differences include additions, deletions or substitutions. Also encompassed by the present invention are nucleic acid sequences that encode analogous polypeptides that exhibit greater, or lesser, biological activity of the TB proteins of the present invention. In particular, the present invention is directed to nucleic acid molecules having at least about 70% (e.g., 75%, 80%, 85%, 90% or 95%) identity with SEQ ID NO: 1, 3, 5, 7, 9, 11, 13, 15, 17, 19, 21, 23, 25, 27, 29, 31, 33, 35, 37, 39, 41, 43, 45, 47, or combinations thereof.

The nucleic acid molecules of the present invention, including the full length sequences, the partial sequences, functional fragments and homologues, once encoded into polypeptides, elicit a specific immunogenic TB response, or has the function of the polypeptide, as further described herein. The homologous nucleic acid sequences can be determined using methods known to those of skill in the art, and by methods described herein including those described for determining homologous polypeptide sequences.

Also encompassed by the present invention are nucleic acid sequences, DNA or RNA, which are substantially complementary to the DNA sequences encoding the antigenic polypeptides of the present invention. Such sequences can be used to design PCR primers to amplify and isolate homologous DNA coding sequences from related *Mycobacteria* spp. The present invention includes sequences those that specifically hybridize under conditions of stringency known to those of skill in the art. As defined herein, substantially complementary means that the nucleic acid need not reflect the exact sequence of the TB sequences, but must be sufficiently similar in sequence to permit hybridization with TB nucleic acid sequence under high stringency conditions. For example, non-complementary bases can be interspersed in a nucleotide sequence, or the sequences can be longer or shorter than the TB nucleic acid sequence, provided that the sequence has a sufficient number of bases complementary to the TB sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

In another embodiment, the present invention includes genomic DNA that has nucleic acid molecules (e.g., probes or primers) that hybridize to the antigenic sequences, SEQ ID NO:1, 3, 5, 7, 9, 11, 13, 15, 17, 19, 21, 23, 25, 27, 29, 31, 33, 35, 37, 39, 41, 43, 45, 47, or combinations thereof under high or moderate stringency conditions. In one aspect, the present invention includes molecules that hybridize or contain at least about 20 contiguous nucleotides or longer in length (e.g., 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000). Such molecules hybridize to one of the TB nucleic acid sequences under high stringency conditions. The present invention includes such molecules and those that encode a polypeptide that has the functions or biological activity described herein.

Typically the nucleic acid probe comprises a nucleic acid sequence (e.g. SEQ ID NO: 1, 3, 5, 7, 9, 11, 13, 15, 17, 19, 21, 23, 25, 27, 29, 31, 33, 35, 37, 39, 41, 43, 45, 47, or combinations thereof) and is of sufficient length and complementarity to specifically hybridize to a nucleic acid sequence that encodes an antigenic polypeptide. For example, a nucleic acid probe can be at least about 5%, 10%, 20%, 30%, 40%, 50%, 60%, 70%, 80% or 90% the length of the TB nucleic acid sequence. The requirements of sufficient length and complementarity can be easily determined by one of skill in the art. Suitable hybridization conditions (e.g., high stringency conditions) are also described herein. Additionally, the present invention encompasses fragments of the polypeptides of the present invention or nucleic acid sequences that encodes a polypeptide wherein the polypeptide has the biologically activity of the polypeptides recited herein.

Such fragments are useful as probes for assays described herein, and as experimental tools, or in the case of nucleic acid fragments, as primers. A preferred embodiment includes primers and probes which selectively hybridize to the nucleic acid constructs encoding any one of the recited polypeptides. For example, nucleic acid fragments which encode any one of the domains described herein are also implicated by the present invention.

Stringency conditions for hybridization refers to conditions of temperature and buffer composition which permit hybridization of a first nucleic acid sequence to a second nucleic acid sequence, wherein the conditions determine the degree of identity between those sequences which hybridize to each other. Therefore, "high stringency conditions" are those conditions wherein only nucleic acid sequences which are very similar to each other will hybridize. The sequences can be less similar to each other if they hybridize under moderate stringency conditions. Still less similarity is needed for two sequences to hybridize under low stringency conditions. By varying the hybridization conditions from a stringency level at which no hybridization occurs, to a level at which hybridization is first observed, conditions can be determined at which a given sequence will hybridize to those sequences that are most similar to it. The precise conditions determining the stringency of a particular hybridization include not only the ionic strength, temperature, and the concentration of destabilizing agents such as formamide, but also factors such as the length of the nucleic acid sequences, their base composition, the percent of mismatched base pairs between the two sequences, and the frequency of occurrence of subsets of the sequences (e.g., small stretches of repeats) within other non-identical sequences. Washing is the step in which conditions are set so as to determine a minimum level of similarity between the sequences hybridizing with each other. Generally, from the lowest temperature at which only homologous hybridization occurs, a 1% mismatch between two sequences results in a 1° C. decrease in the melting temperature ($T_m$) for any chosen SSC concentration. Generally, a doubling of the concentration of SSC results in an increase in the $T_m$ of about 17° C. Using these guidelines, the washing temperature can be determined empirically, depending on the level of mismatch sought. Hybridization and wash conditions are explained in Current Protocols in Molecular Biology (Ausubel, F. M. et al., eds., John Wiley & Sons, Inc., 1995, with supplemental updates) on pages 2.10.1 to 2.10.16, and 6.3.1 to 6.3.6.

High stringency conditions can employ hybridization at either (1) 1×SSC (10×SSC=3 M NaCl, 0.3 M Na$_3$-citrate ... 2H$_2$O (88 g/liter), pH to 7.0 with 1 M HCl), 1% SDS (sodium dodecyl sulfate), 0.1-2 mg/ml denatured calf thymus DNA at 65° C., (2) 1×SSC, 50% formamide, 1% SDS, 0.1-2 mg/ml denatured calf thymus DNA at 42° C., (3) 1% bovine serum albumin (fraction V), 1 mM Na$_2$ ... EDTA, 0.5 M NaHPO$_4$ (pH 7.2) (1 M NaHPO$_4$=134 g Na$_2$HPO$_4$ ... 7H$_2$O, 4 ml 85% H$_3$PO$_4$ per liter), 7% SDS, 0.1-2 mg/ml denatured calf thymus DNA at 65° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured calf thymus DNA at 42° C., (5) 5×SSC, 5×Denhardt's solution, 1% SDS, 100 µg/ml denatured calf thymus DNA at 65° C., or (6) 5×SSC, 5×Denhardt's solution, 50% formamide, 1% SDS, 100 µg/ml denatured calf thymus DNA at 42° C., with high stringency washes of either (1) 0.3-0.1×SSC, 0.1% SDS at 65° C., or (2) 1 mM Na$_2$EDTA, 40 mM NaHPO$_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6(log$_{10}$ M)+0.41(% G+C)−0.61 (% formamide)−500/L), where "M" is the molarity of monovalent cations (e.g., Na$^+$), and "L" is the length of the hybrid in base pairs.

Moderate stringency conditions can employ hybridization at either (1) 4×SSC, (10×SSC=3 M NaCl, 0.3 M Na$_3$-citrate ... 2H$_2$O (88 g/liter), pH to 7.0 with 1 M HCl), 1% SDS (sodium dodecyl sulfate), 0.1-2 mg/ml denatured calf thymus DNA at 65° C., (2) 4×SSC, 50% formamide, 1% SDS, 0.1-2 mg/ml denatured calf thymus DNA at 42° C., (3) 1% bovine serum albumin (fraction V), 1 mM Na$_2$ ... EDTA, 0.5 M NaHPO$_4$ (pH 7.2) (1 M NaHPO$_4$=134 g Na$_2$HPO$_4$ ... 7H$_2$O, 4 ml 85% H$_3$PO$_4$ per liter), 7% SDS, 0.1-2 mg/ml denatured calf thymus DNA at 65° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured calf thymus DNA at 42° C., (5) 5×SSC, 5×Denhardt's solution, 1% SDS, 100 µg/ml denatured calf thymus DNA at 65° C., or (6) 5×SSC, 5×Denhardt's solution, 50% formamide, 1% SDS, 100 µg/ml denatured calf thymus DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6(log$_{10}$ M)+0.41(% G+C)−0.61 (% formamide)−500/L), where "M" is the molarity of monovalent cations (e.g., Na+), and "L" is the length of the hybrid in base pairs.

Low stringency conditions can employ hybridization at either (1) 4×SSC, (10×SSC=3 M NaCl, 0.3 M Na$_3$-citrate ... 2H$_2$O (88 g/liter), pH to 7.0 with 1 M HCl), 1% SDS (sodium dodecyl sulfate), 0.1-2 mg/ml denatured calf thymus DNA at 50° C., (2) 6×SSC, 50% formamide, 1% SDS, 0.1-2 mg/ml denatured calf thymus DNA at 40° C., (3) 1% bovine serum albumin (fraction V), 1 mM Na$_2$ ... EDTA, 0.5 M NaHPO$_4$ (pH 7.2) (1 M NaHPO$_4$=134 g Na$_2$HPO$_4$ ... 7H$_2$O, 4 ml 85% H$_3$PO$_4$ per liter), 7% SDS, 0.1-2 mg/ml denatured calf thymus DNA at 50° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured calf thymus DNA at 40° C., (5) 5×SSC, 5×Denhardt's solution, 1% SDS, 100 µg/ml denatured calf thymus DNA at 50° C., or (6) 5×SSC, 5×Denhardt's solution, 50% formamide, 1% SDS, 100 µg/ml denatured calf thymus DNA at 40° C., with low stringency washes of either 2×SSC, 0.1% SDS at 50° C., or (2) 0.5% bovine serum albumin (fraction V), 1 mM Na$_2$EDTA, 40 mM NaHPO$_4$ (pH 7.2), 5% SDS. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in °C.=(2×the number of A and T bases)+(4×the number of G and C bases). For hybrids believed to be about 18 to about 49 base pairs in length, the $T_m$ in °C.=(81.5° C.+16.6($\log_{10}$ M)+0.41(% G+C)−0.61 (% formamide)−500/L), where "M" is the molarity of monovalent cations (e.g., Na.+), and "L" is the length of the hybrid in base pairs.

Immunogenic antigens can be produced recombinantly using a DNA sequence that encodes the antigen, which has been inserted into an expression vector and expressed in an appropriate host cell. DNA sequences encoding antigens can, for example, be identified by screening an appropriate genomic or cDNA expression library with sera obtained from patients infected with *M. tuberculosis*, HIV, *Plasmodium, Leishmania*, herpes virus, or hepatitis virus. Such screens can generally be performed using techniques well known to those of ordinary skill in the art. For example, using oligonucleotide primers designed from above DNA sequences, PCR can be employed to isolate a gene from a cDNA or genomic library.

Alternatively, genomic or cDNA libraries derived from *M. tuberculosis*, HIV, *Plasmodium, Leishmania*, herpes virus, or hepatitis virus can be screened directly using peripheral blood mononuclear cells (PBMCs) or T cell lines or clones derived from one or more immune individuals. In general, PBMCs and/or T cells for use in such screens can be prepared as described below. Direct library screens can generally be performed by assaying pools of expressed recombinant proteins for the ability to induce proliferation and/or interferon production in T cells derived from an immune individual.

The invention also provides vectors, plasmids or viruses containing one or more of the nucleic acid molecules (e.g., having the sequence of SEQ ID NO:1, 3, 5, 7, 9, 11, 13, 15, 17, 19, 21, 23, 25, 27, 29, 31, 33, 35, 37, 39, 41, 43, 45, 47, or combinations thereof). Suitable vectors for use in eukaryotic and prokaryotic cells are known in the art and are commercially available or readily prepared by a skilled artisan.

EXEMPLIFICATION

Example 1

To generate recombinant *S. mitis* (rS. mitis), it was first established that strain NCTC 12261 could be transformed and could express foreign genes. The strategy was to express foreign vaccine antigens in the secreted form, which is necessary for bacterial-expressed antigens to be immunogenic. Thus far the genes encoding *M. tuberculosis* Ag85b and HIV-1 HXBc2 env-His-tag in-frame have been successfully integrated in the genome of *S. mitis*. These genes were synthetically produced and had with codons optimized for *S. mitis*. The genes integrated at the 5' end of the pullulanase gene (pulA/Smt0163) encoding a signal peptide that allows processing and secretion of the *M. tuberculosis* and HIV antigens. FIG. 2 illustrates this integration strategy. The signal peptide has an amino-terminal region (N), a hydrophobic core (H), a signal peptidase cleavage site (C), and an accessory Sec transport motif (AST). For stable expression, the *M. tuberculosis* Antigen 85b and HIV HXBc2 genes or the ermR cassette were integrated via homologous recombination into the pulA gene of *S. mitis*. PulA was selected as the integration site because the gene has a strong promoter and encodes localization motifs for the gene product; furthermore pulA was not essential for bacterial growth. A DNA fragment containing ermR alone (control) or HIV and ermR or 85b and ermR flanked by 250 bp pulA 5' and 3' fragments was constructed and ligated into a suicide vector (pCR2.1) for transformation and integration at the pulA locus (FIG. 3A). *S. mitis* transformants were selected on erythromycin-containing plates. To test whether a foreign gene was integrated into *S. mitis* a genomic PCR analysis was performed. PCR analysis showed that the *S. mitis*-specific primers A/B generated the expected 250 bp smt0163 PCR product, while the HIV-specific primer C and ermR-specific primer D generated the expected 1 kb product (FIG. 4). In addition, *S. mitis* pulA specific primer X and 85b-specific primer y generated the expected 250 bp product (FIG. 5, lanes 2-3).

Next, the expression of Env antigen in *S. mitis* using the C-terminal His-tag fused to HIV antigen for detection was determined. An expression cassette containing the HIV gene was then transformed into *S. mitis* for homologous recombination into the pulA gene. *S. mitis* vaccine vector candidates were grown to mid-log phase in Todd-Hewitt Broth medium with erythromycin. Proteins from cell lysates (1 μg) and from concentrated supernatants (10 ml) were size fractionated by SDS-PAGE. HIV HXBc2 gp120 (Env) in the bacterial pellets and as a secreted product in the supernatants was detected by Western blotting using horseradish peroxidase conjugated anti-His tag antibody (Penta-His, Qiagen) and a chemiluminescence substrate (Invitrogen). HIV Env linked to the PulA signal peptide was expressed in *S. mitis* cell lysates of a representative recombinant clone (FIGS. 6A and 6B). Lysates also contained proteins that crossreact with the anti-His-tag antibody (FIG. 6A). In addition, secreted Env was detected in bacterial culture supernatants (FIG. 5C). 100 ng of His-tagged *M. tuberculosis* protein (MT0401) was used as a positive control (FIGS. 6B and 6C, lane 1). The arrow denotes the Env protein band present in the TCA-precipitated (FIG. 5C, lane 2) and Amicon-concentrated supernatant (FIG. 6C, lane 4), although not in acetone precipitates (FIG. 6C, lane 3). As expected, the HIV Env was not expressed in culture supernatants of parent *S. mitis* cells (FIG. 6C, lanes 5-7). The apparent molecular weight was similar to the expected molecular weight (of approximately 70 kDa), suggesting that Env was not glycosylated in *S. mitis.*

Recombinant *S. mitis* vector is stable after serial passages in vitro. To determine the stability of the integrated Env gene in *rS. mitis*, four clones were picked at random and grown anaerobically for 24 hours which represents approximately three generations (7.1 hours per generation) in Todd-Hewitt Broth (THB) without erythromycin. Cultures were diluted and grown for another 24 hours for a total of approximately 6 generations. Cultures were diluted again and grown on THB plates without erythromycin. From these plates, between 100 and 150 colonies were picked at random and streaked to THB plates with and without erythromycin. This procedure was repeated to measure the stability of the rS. mitis clones over approximately 30 generations on plates with and without antibiotic. Loss of erythromycin-resistance was taken as an indication of the loss of the Env transgene. The progeny from all four clones were stable, with no loss of erythromycin resistance after ten subcultures or 30 generations of replication without antibiotic (FIG. 7A). In addition, the expression of Env in the same daughter clones was analyzed. Western blot analysis revealed that they secreted the same amount of Env antigen as the original *rS. mitis* clones; Env production in a representative daughter clone after 30 generations and the original HIVgp120A clone is shown (FIG. 7B). These results indicate that the resulting *rS. mitis* is stable, a property that makes it a strong candidate for further preclinical testing in animal models.

In summary, it was shown that *S. mitis* can undergo integrative transformation and that the progenies express HIV-1 Env antigen and are highly stable. These results demonstrate that a stable gene expression system in *S. mitis* for constructing an *rS. mitis* vaccine vector we have successfully developed.

*rS. mitis* elicits HIV-specific immune responses in mice. 6-week old Balb/c mice (4 mice per group) were inoculated i.p. twice (four weeks apart) with $10^8$ cfu live *rS. mitis* expressing the HIV-1 HXBc2 Env protein (*rS. mitis* HIVEnv), *S. mitis* with an intergrated ermr gene only (*rS. mitis* sham) or saline (Saline). One week following the second inoculation, mice were bled retrorbitally to isolate peripheral blood mononuclear cells (PBMC) which were then stimulated with either 5 μg/ml *S. mitis* soluble lysate or 5 μg/ml recombinant HXBc2 protein in vitro. Intracellular cytokine staining (ICS) was performed as previously described to assess T cell responses (7). Using the Flowjo software 7.6.3 (Tree Star), IFNγ+, TNFα+, IL-2+, CD4+ or CD8+ T cells were determined, and results from a representative mouse from each group is shown (FIGS. 8 and 9). The Student's t test was used to determine cytokine response difference between the groups and a P value<0.5 was considered significant. ICS analysis revealed that that PBMC from mice vaccinated with the *rS. mitis* HIVEnv had statistically significant higher CD4 T cell responses specific to *S. mitis* lysate antigens compared to saline injected animals (Saline), producing more IFNγ (P<0.003), TNFα (P<0.02) and IL-2 (P<0.002) (FIG. 6). The *rS. mitis* HIVEnv-vaccine group also generated higher frequency *S. mitis* specific-CD8 T cells producing IFNγ (P<0.02), and TNFα (P<0.004) and IL-2 (P<0.005) compared to the saline group (FIG. 8). With respect to HIV-specific T cell responses, the *rS. mitis* HIVEnv vaccinees produced marked higher CD4 and CD8 T cell responses specific to the HIV envelope protein compared *rS. mitis* sham vaccine group. *rS. mitis* HIVEnv vaccinated mice generated higher frequency HIV Env-specific-CD4 T cell producing IFNγ (P<0.005), TNFα (P<0.02 and IL-2 (P<0.01) as well as HIV-specific-CD8 T cells producing IFNγ (P<0.009), TNFα (P<0.03) and IL-2 (P<0.002) compared to *rS. mitis* sham-immunized mice (FIG. 9). Interestingly, *rS. mitis* was capable of inducing CD8 T cell responses in mice, which were detected after in vitro stimulation with *S. mitis* lysate and full-length recombinant protein, which suggests that exogenous *S. mitis* and HIV Env antigens were processed for crosspriming of CD8 T cells (12,16). This proof of concept immunogenicity study shows that *rS. mitis* can induce *S. mitis*- and HIV-specific cellular immunity.

Example 2

Two candidate secretion/cell-wall anchored systems will be tested for the expression of the HIV inhibitor, T20. Both the serine-rich GspB-homologue or the pullulanase protein expressed in *S. mitis* will be tested. Both proteins contain an N-terminal signal peptide (YSIRK type) for secretion and the LPXTG motif for cell-wall surface expression. The signal peptide determinants for secretion of GspB into culture supernatants are the amino-terminal region (N), a hydrophobic core (H), a signal peptidase cleavage site (C), and the accessory Sec transport (AST). Interestingly, attachment of the signal peptide region but exclusion of the LPXTG sequence results in secretion of GspB in culture supernatants. Hence, *S. mitis* expressing HIV proteins on the cell wall surface will be constructed by flanking the viral protein with the signal peptide and the LPXTG anchor, and *S. mitis*-secreting HIV proteins or T20 inhibitor by attaching the signal peptide to the N-terminus.

A recombinant *S. mitis* secreting an HIV-1 inhibitor will be constructed as a microbicide since it was hypothesized that inhibiting HIV entry into oral mucosal target cells will be a viable approach for preventing mother-to-child transmission. Recombinant *S. mitis* secreting the potent HIV peptide inhibitor, T20, will be constructed. T20 is a 36-amino acid peptide (YTSLIHSLIEESQNQQEKNEQELLELDKWASLWNWF (SEQ ID NO: 53)) that acts as a decoy α-helix and prevents HIV-1 infection by disrupting the assembly of the six-helix bundle viral fusion apparatus by mimicking the heptad repeat 2 (HR2) oligomerization domain of the gp41 envelope glycoprotein. T20 is clinically proven to inhibit a diversity of primary isolates of HIV-1 in humans. However, its delivery as a synthetic peptide is associated with high cost and inconvenient dosing regimen, making this drug a reserve in patients with drug resistant HIV. Delivery of this HIV inhibitor in the most cost-effective way will be highly beneficial, and the approach to accomplish this is to deliver the T20 inhibitor as an oral microbicide. Recombinant *S. mitis* secreting T20 which can be administered orally will be generated. The T20 peptide will be attached to N-terminal signal peptide of *S. mitis* pullulanase or GspB protein homologue, and an IgA1 protease cleavage site will be added to generate free T20 peptides. Engineered constructs will then be tested for the ability to secrete T20 that will inhibit HIV using the standard neutralization assay (Cayabyab M, Karlsson G B, Etemad-Moghadam B A, Hofmann W, Steenbeke T, Halloran M, Fanton J W, Axthelm M K, Letvin N L, Sodroski J G: Changes in human immunodeficiency virus type 1 envelope glycoproteins responsible for the pathogenicity of a multiply passaged simian-human immunodeficiency virus (SHIV-HXBc2). J Virol 1999, 73:976-984).

Example 3

Other commensal bacteria that encode a vaccine antigen can be generated by using the genbank sequences below for the construction of a DNA fragment containing erythromycin resistance cassette that is flanked by 250 bp pulA 5' and 3' fragments and ligating it into a suicide vector (pCR2.1) for transformation and integration at the pulA locus.

The genome of type strain *S. mitis* NCTC 12261 was sequenced and genbank numbers can be accessed via pubmed. The Genbank # of *S. mitis* sequence is as follows:

*Streptococcus mitis* NCTC 12261 contig1, whole genome shotgun sequence 113,379 bp linear DNA Accession: AEDX01000011.1GI:307615963 (SEQ ID NO: 55)
*Streptococcus mitis* NCTC 12261 contig2, whole genome shotgun sequence 24,459 bp linear DNA Accession: AEDX01000017.1GI:307615908 (SEQ ID NO: 56)
*Streptococcus mitis* NCTC 12261 contig3, whole genome shotgun sequence 81,409 bp linear DNA Accession: AEDX01000018.1GI:307615827 (SEQ ID NO: 57)
*Streptococcus mitis* NCTC 12261 contig4, whole genome shotgun sequence 314,111 bp linear DNA Accession: AEDX01000019.1GI:307615569 (SEQ ID NO: 58)
*Streptococcus mitis* NCTC 12261 contig5, whole genome shotgun sequence 100,480 bp linear DNA Accession: AEDX01000020.1GI:307615480 (SEQ ID NO: 59)
*Streptococcus mitis* NCTC 12261 contig6, whole genome shotgun sequence 91,167 bp linear DNA Accession: AEDX01000021.1GI:307615386 (SEQ ID NO: 60)
*Streptococcus mitis* NCTC 12261 contig7, whole genome shotgun sequence 84,457 bp linear DNA Accession: AEDX01000022.1GI:307615313 (SEQ ID NO: 61)
*Streptococcus mitis* NCTC 12261 contig8, whole genome shotgun sequence 111,153 bp linear DNA Accession: AEDX01000023.1GI:307615211 (SEQ ID NO: 62)

*Streptococcus mitis* NCTC 12261 contig9, whole genome shotgun sequence 112,014 bp linear DNA Accession: AEDX01000024.1GI:307615105 (SEQ ID NO: 63)
*Streptococcus mitis* NCTC 12261 contig10, whole genome shotgun sequence 88,437 bp linear DNA Accession: AEDX01000001.1GI:307616687 (SEQ ID NO: 64)
*Streptococcus mitis* NCTC 12261 contig11, whole genome shotgun sequence 93,022 bp linear DNA Accession: AEDX01000002.1GI:307616595 (SEQ ID NO: 65)
*Streptococcus mitis* NCTC 12261 contig12, whole genome shotgun sequence 71,904 bp linear DNA Accession: AEDX01000003.1GI:307616529 (SEQ ID NO: 66)
*Streptococcus mitis* NCTC 12261 contig13, whole genome shotgun sequence 164,416 bp linear DNA Accession: AEDX01000004.1GI:307616373 (SEQ ID NO: 67)
*Streptococcus mitis* NCTC 12261 contig14, whole genome shotgun sequence 75,285 bp linear DNA Accession: AEDX01000005.1GI:307616290 (SEQ ID NO: 68)
*Streptococcus mitis* NCTC 12261 contig15, whole genome shotgun sequence 16,944 bp linear DNA Accession: AEDX01000006.1GI:307616272 (SEQ ID NO: 69)
*Streptococcus mitis* NCTC 12261 contig16, whole genome shotgun sequence 112,411 bp linear DNA Accession: AEDX01000007.1GI:307616176 (SEQ ID NO: 70)
*Streptococcus mitis* NCTC 12261 contig17, whole genome shotgun sequence 22,040 bp linear DNA Accession: AEDX01000008.1GI:307616156 (SEQ ID NO: 71)
*Streptococcus mitis* NCTC 12261 contig18, whole genome shotgun sequence 124,845 bp linear DNA Accession: AEDX01000009.1GI:307616054 (SEQ ID NO: 72)
*Streptococcus mitis* NCTC 12261 contig19, whole genome shotgun sequence 2,436 bp linear DNA Accession: AEDX01000010.1GI:307616052 (SEQ ID NO: 73)
*Streptococcus mitis* NCTC 12261 contig20, whole genome shotgun sequence 8,218 bp linear DNA Accession: AEDX01000012.1GI:307615955 (SEQ ID NO: 74)
*Streptococcus mitis* NCTC 12261 contig21, whole genome shotgun sequence 5,961 bp linear DNA Accession: AEDX01000013.1GI:307615946 (SEQ ID NO: 75)
*Streptococcus mitis* NCTC 12261 contig22, whole genome shotgun sequence 4,520 bp linear DNA Accession: AEDX01000014.1GI:307615941 (SEQ ID NO: 76)
*Streptococcus mitis* NCTC 12261 contig23, whole genome shotgun sequence 3,240 bp linear DNA Accession: AEDX01000015.1GI:307615936 (SEQ ID NO: 77)
*Streptococcus mitis* NCTC 12261 contig24, whole genome shotgun sequence 4,773 bp linear DNA Accession: AEDX01000016.1GI:307615932 (SEQ ID NO: 78)
*Streptococcus mitis* NCTC 12261, whole genome shotgun sequencing project 1,831,081 bp other DNA. This entry is the master record for a whole genome shotgun sequencing project and contains no sequence data. Accession: NZ_AEDX00000000.1GI:307708845

*Streptococcus mitis* NCTC 12261, whole genome shotgun sequencing project 24 rc linear DNA. This entry is the master record for a whole genome shotgun sequencing project and contains no sequence data. Accession:AEDX00000000.1GI:307616765

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09376686B2). An electronic copy of the "Sequence Listing" will also be available from the USPTO upon request and payment of the fee set forth in 37 CFR 1.19(b)(3).

---

What is claimed is:

1. An integrally transformed non-pathogenic, commensal bacterium that expresses a synthetic nucleic acid molecule of a foreign fusion polypeptide therein, wherein the synthetic nucleic acid molecule that encodes the foreign fusion polypeptide is stably integrated into genomic DNA of the bacterium, wherein the bacterium is *Streptococcus mitis*, wherein the synthetic nucleic acid molecule comprises a HIV gp120/pullulanase having SEQ ID NO: 51, and wherein the foreign fusion polypeptide comprises a HIV gp120/pullulanase fusion having SEQ ID NO: 52.

2. The integrally transformed non-pathogenic, commensal bacterium of claim 1, wherein the synthetic nucleic acid molecule of the foreign fusion polypeptide elicits an immunogenic response in an individual.

3. The integrally transformed non-pathogenic, commensal bacterium of claim 1, wherein the HIV gp120/pullulanase is expressed in the cytoplasm, or exports to the surface of the bacterium.

4. The integrally transformed non-pathogenic, commensal bacterium of claim 2, wherein the non-pathogenic, commensal bacterium expresses the HIV gp120/pullulanase in the cytoplasm or secretes the HIV gp120/pullulanase on the surface of the bacterium.

5. A fusion polypeptide comprising SEQ ID NO: 52.

* * * * *